United States Patent [19]

Poindexter et al.

[11] Patent Number: 5,635,503
[45] Date of Patent: Jun. 3, 1997

[54] DIHYDROPYRIDINE NPY ANTAGONISTS: PIPERAZINE DERIVATIVES

[75] Inventors: Graham S. Poindexter, Old Saybrook; Marc Bruce, Wallingford; Graham Johnson, Madison, all of Conn.; Michael Kozlowski, Palo Alto, Calif.; Karen LeBoulluec, Wallingford; Ivo Monkovic, Durham, both of Conn.; Ramakrishna Seethala, Cranbury, N.J.; Charles P. Sloan, Wallingford, Conn.

[73] Assignee: Bristol-Myers Squibb Company, Princeton, N.J.

[21] Appl. No.: 482,355

[22] Filed: Jun. 7, 1995

[51] Int. Cl.$^6$ .......................... A61K 31/435; A61K 31/55; C07D 401/12; C07D 413/14
[52] U.S. Cl. .......................... 514/218; 514/252; 540/575; 544/364; 544/365
[58] Field of Search .......................... 540/575; 544/364, 544/365; 514/218, 252

[56] References Cited

U.S. PATENT DOCUMENTS

| | | | |
|---|---|---|---|
| 4,755,512 | 7/1988 | Poindexter et al. | 514/252 |
| 4,829,076 | 5/1989 | Szilagyi et al. | 514/356 |
| 4,868,181 | 9/1989 | Johnson et al. | 514/252 |
| 5,166,147 | 11/1992 | Earl | 514/252 |
| 5,166,148 | 11/1992 | Aldrich et al. | 514/252 |

FOREIGN PATENT DOCUMENTS 0060674  9/1982  European Pat. Off. .

OTHER PUBLICATIONS

Aritomi et al, *Chem. Pharm. Bull.*, 28 (11), 3163–71 (1980).

*Primary Examiner*—Philip I. Datlow
*Attorney, Agent, or Firm*—Richard P. Ryan

[57] ABSTRACT

A series of non-peptidergic antagonists of NPY have been synthesized and are comprised of piperazine and homopiperazine derivatives of 4-phenyl-1,4-dihydropyridines of Formula (I).

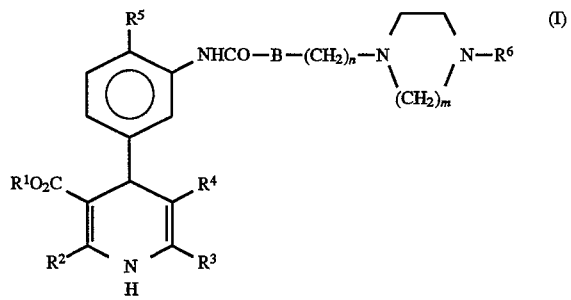

As antagonists of NPY-induced feeding behavior, these compounds are expected to act as effective anorexiant agents in promoting weight loss and treating eating disorders.

10 Claims, No Drawings

DIHYDROPYRIDINE NPY ANTAGONISTS: PIPERAZINE DERIVATIVES

BACKGROUND OF THE INVENTION

The present invention concerns heterocyclic carbon compounds comprising 4-phenyl-1,4-dihydropyridines with a piperazinyl- or homopiperazinyl-containing moiety attached to the 3-position of the 4-phenyl ring. These compounds act as NPY antagonists. As such they should represent a class of improved anorexiants lacking some of the side-effects possessed by currently available anorexiants.

A substantial body of art has accumulated over the past two decades with respect to 4-aryl-1,4-dihydropyridine compounds. A large number of these possess calcium antagonist properties and find utility in the treatment of cardiovascular diseases.

Earlier work from these laboratories involved a series of 4-aryl-dihydropyridine cardiovascular agents, including compounds of formula (1), which were

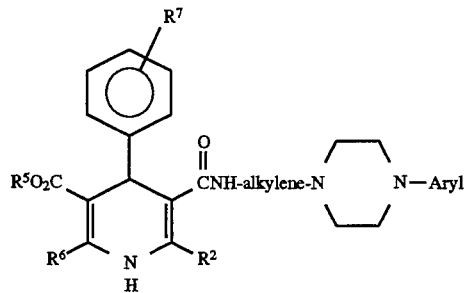

(1)

disclosed and claimed in U.S. Pat. No. 4,755,512.

Additionally, 1,4-dihydropyridine compounds have been disclosed that have an arylpiperazine system attached by an alkyl or alkoxyalkyl chain to the $R^2$-position of the dihydropyridine ring. Aritomi, et al., in *Chem. Pharm. Bull.*, 28 (11), 3163–71 (1980) disclose compounds having an alkylenylpiperazine group at the 2-position of the dihydropyridine nucleus, e.g.

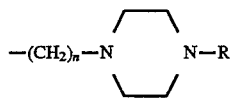

wherein n=2 and R is alkyl, aryl, or arylalkyl. Specifically disclosed is compound (2).

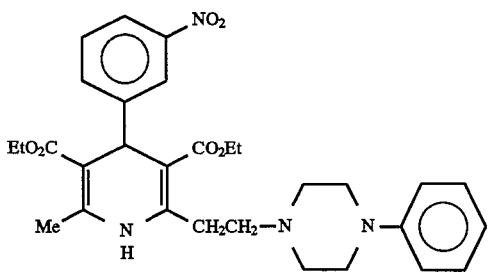

(2)

European Patent Application 60,674, published in 1982, discloses anti-ischemic and antihypertensive agents of structure (3)

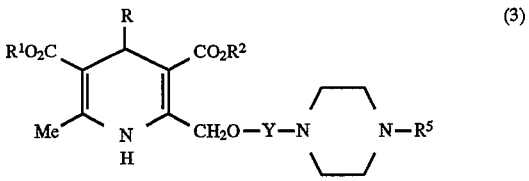

(3)

wherein Y is an ethylene or propylene chain; $R^5$ is $C_{1-4}$ alkyl, aryl, arylalkyl, and the like.

These reference compounds are easily distinguished structurally from the compounds of the instant invention by virtue of being attached to the dihydropyridine ring as well as by the nature of the linking functional group, e.g. alkylenyl, alkylene-oxo-alkylenyl, and carboxamido groups. In contrast, compounds of the instant invention contain an alkylenylpiperazine moiety attached to the 4-phenyl ring by means of an urea or anilide connection. Not only are the present compounds structurally novel, they also have been discovered to possess novel NPY antagonist activity.

Neuropeptide Y (NPY) is a 36 amino acid peptide first isolated in 1982 from porcine brain.[1,2] The peptide is a member of a larger peptide family which also includes peptide YY (PYY), pancreatic peptide (PP), and the non-mammalian fish pancreatic peptide Y (PY). Neuropeptide Y is very highly conserved in a variety of animal, reptile and fish species. It is found in many central and peripheral sympathetic neurons and is the most abundant peptide observed in the mammalian brain. In the brain, NPY is found most abundantly in limbic regions. The peptide has been found to elicit a number of physiological responses including appetite stimulation, anxiolysis, hypertension, and the regulation of coronary tone.

Structure-activity studies with a variety of peptide analogs (fragments, alanine replacements, point mutations, and internal deletion/cyclized derivatives) suggest a number of receptor subtypes exist for NPY.[2b] These currently include the $Y_1$, $Y_2$, $Y_3$, and the $Y_{1-like}$ or $Y_4$ subtypes.

Although a number of specific peptidic antagonists have been identified for most of the subtypes, few selective non-peptidic antagonists have been reported to date. Examples of these antagonists are displayed in Charts 1 and 2. The heterocyclic guanidine derivative He 90481 (4) was found to be a weak but competitive antagonist of NPY-induced $Ca^{++}$ entry in HEL cells ($pA_2$=4.43).[3] The compound was also found to have $\alpha_2$-adrenergic and histaminergic activity at this dose range. D-Myo-inositol-1,2,6-triphosphate (5) was reported to be a potent but non-competitive antagonist to NPY-induced contractions in guinea pig basilar artery.[4] Similarly, the benextramine-like bisguanidines 6a and 6b were reported to displace $^3$H-NPY in rat brain ($IC_{50}$, 19 and 18.4 µM) and to display functional antagonism in rat femoral artery.[5] The bisguanidine 6b was shown to be functionally selective for the $Y_2$ receptor since it antagonized the effect of the $NPY_2$ agonist $NPY_{13-36}$ but had no effect on the vasoconstrictive activity of the $NPY_1$ agonist [$Leu^{31}$, $Pro^{34}$]NPY.[5c]

Compound (7), BIBP 3226[6], displaces I-125 Bolton-Hunter labeled NPY in human neuroblastoma cells (SK-N-MC). Compound (7) antagonized the NPY-induced increase in intracellular $Ca^{++}$ in SK-N-MC cells as well as antagonizing the NPY-induced pressor response in pithed rat experiments.

In addition to displacing I-125 labeled NPY and PYY in human neuroblastoma cells, compound (8), SR 120819A[7], also antagonized NPY-related increases in diastolic blood pressure in an anesthetized guinea pig model.

In sum, the compounds of this invention may be distinguished over compounds of the prior art on the basis of molecular structure and biologic activity. There is nothing in the prior art that anticipates or suggests the novel NPY antagonists of the present invention.

SUMMARY AND DETAILED DESCRIPTION OF THE INVENTION

The present invention comprises the compounds of Formula (I),

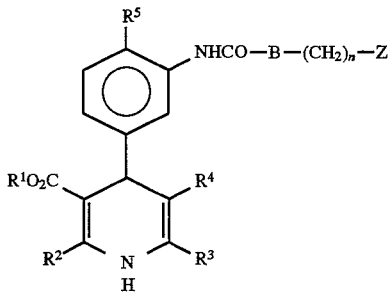

their pharmaceutically acceptable acid addition salts and/or their hydrates thereof. In the foregoing structural formula, the symbols $R^1$–$R^5$, B and Z have the following meanings.

$R^1$ is lower alkyl; methyl being preferred.

$R^2$ and $R^3$ are independently selected from cyano and lower alkyl, with methyl being preferred.

$R^4$ is selected from —$CO_2R^1$, cyano and

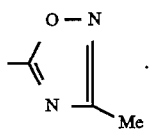

$R^5$ can be hydrogen, halogen, hydroxy, lower alkyl, lower alkoxy, and lower alkenyloxy such as allyloxy.

B is NH or a chemical bond.

The symbol n is an integer from 2 to 5 with 3 being preferred.

Finally, Z is

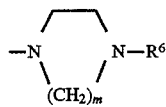

wherein m is an integer of 2 or 3 and $R^6$ can be formyl, lower alkyl, phenyl-lower alkyl,

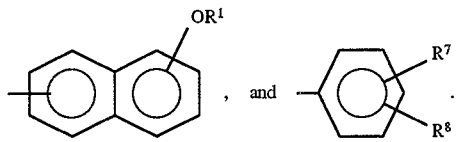

The phenyl ring substituents $R^7$ and $R^8$ are independently selected from hydrogen, lower alkyl, $C_{3-7}$ cycloalkyl, lower alkoxy, hydroxy, phenoxy, $NH_2$, $NHCOR^1$, $CO_2R^1$, $NO_2$, trifluoromethyl and phenyl.

The term "lower" indicates that the alkyl, alkoxy, or alkenyloxy group contains from one to four carbon atoms. Preferred compounds of the instant invention are Formula (I) compounds wherein $R^2$ and $R^3$ are methyl; $R^4$ is —$CO_2Me$; $R^5$ is hydrogen; B is NH; and $R^6$ is an aromatic ring-containing moiety. Most preferred compounds are those wherein $R^6$ is substituted phenyl, particularly with alkoxy substituents.

The compounds of the present invention can exist as optical isomers and both the racemic mixtures of these isomers as well as the individual optical isomers themselves are within the scope of the present invention. The racemic mixtures can be separated into their individual isomers through well known techniques such as the separation of the diastereomeric salts formed with optically active acids, followed by conversion back to the optically active bases.

As indicated, the present invention also pertains to the pharmaceutically acceptable non-toxic salts of these basic compounds. Such salts include those derived from organic and inorganic acids such as, without limitation, hydrochloric acid, hydrobromic acid, phosphoric acid, sulfuric acid, methanesulfonic acid, acetic acid, tartaric acid, lactic acid, succinic acid, citric acid, maleic acid, fumaric acid, sorbic acid, aconitic acid, salicylic acid, phthalic acid, enanthic acid, and the like.

The compounds of the present invention may be produced by the following processes which employ variations of the Hantzsch synthetic reaction applied to the appropriate starting materials. General processes for preparing Formula (I) compounds are outlined in Schemes 1 and 2. The symbols $R^1$–$R^6$, B, n and m are as previously defined, and X is chloro or bromo. The dihydropyridine intermediate (V) can be prepared by the reaction of 3-nitrobenzaldehyde and the requisite acetoacetates, such as compound (VI) wherein $R^4$ is e.g. carbethoxy, under standard Hantzsch condensation conditions[8] (e.g. ammonium acetate in refluxing isopropanol) if symmetrical intermediates of Formula (V) are desired. Symmetrical intermediate (V) compounds would have $R^2=R^3$ and $R^4$=—$CO_2R^1$. Unsymmetrical dihydropyridines (V) are obtained using modified Hantzsch conditions starting with Knoevenagel adducts (VII)[9] and the appropriate dicarbonyl compounds (VI). A number of these dihydropyridines (V) have been described in the literature.[10] Reduction of intermediate (V) compounds catalytically or by using either an iron method (Fe/$NH_4Cl$/aq. EtOH) or a Ni(OAc)$_2$/NaBH$_4$ exchange resin procedure[11] provides the amino intermediates (IV). A number of these aniline derivatives have also been described in the literature[12] Scheme 1 illustrates their conversion into anilide-linked Formula (I) compound. Reaction of (IV) with a haloacyl halide (VIII) gives compound (III), and subsequent treatment with the piperazinyl or homopiperazinyl compounds (X) yields the desired Formula (I) products.

Syntheses of Formula (I) compounds containing urea linkages are shown in Scheme 2. In process A, the aniline intermediate (IV) is reacted with an appropriate haloalkyl isocyanate (IX) to produce intermediate compound (II) which is then further reacted with piperazine intermediate (X) to yield urea-linked Formula (I) product. Process B involves the conversation of the aniline intermediate (IV) to an isocyanate intermediate (XXXIV) via the carbamate intermediate (XXIV). Reaction of the isocyanate compound (XXXIV) with an aminoalkyl piperidine or tetrahydropyridine compound (XX) gives the urea-linked Formula (I) product in good overall yield.

Certain intermediates of Formula (V) require modified syntheses and some of these are exemplified in Scheme 3. Synthesis A shows hydrolysis of an acetal derivative (XIII) following a general synthetic route similar to that reported by Satoh[13]. Hydrolysis of the acetal (XIII) was accomplished by acid treatment (HCl/acetone). The resulting aldehyde (XII) was converted to the oxime derivative via reaction with hydroxylamine in acetic acid and then was dehydrated by heating in acetic anhydride to produce the cyano-substituted intermediate (V). Conversion of a cyano-substituted nitrobenzene compound (V) to the cyano-substituted aniline intermediate (IV) is accomplished with Fe/NH$_4$Cl in ethanol.

Synthesis B of Scheme 3 outlines preparation of oxadiazole substituted intermediates. A dihydropyridine carboxylic acid starting material (XIV) is coupled with acetamidoxime via carbonyldiimidazole (CDI) and then heated at about 200° to convert the intermediary oxime ester to the oxadiazole nitro compound (V). Reduction of (V) to the oxadiazole substituted aniline compound (IV) is carried out using the iron method in order to preclude N—O bond cleavage seen with hydrogenolysis.

For products wherein $R^5$ is other than hydrogen, the reaction sequence begins using the appropriate $R^5$-substituted nitrobenzaldehyde except when $R^5$ is hydroxy. In this case, compound (V), wherein $R^5$ is hydroxy, is O-allylated by treatment with NaH/allyl bromide to give an intermediate (V) wherein $R^5$ is allyloxy, as shown in Scheme 4, process A. Iron reduction provides the aniline intermediate (IV) which is reacted sequentially with an appropriate haloalkyl isocyanate or haloacyl halide followed by a piperazine or homopiperazine reactant to provide the Formula (I) compound wherein $R^5$ is allyloxy. Deprotection is achieved using PdCl$_2$ in a HOAc/NaOAc buffer to yield the $R^5$-OH Formula (I) product.

Substituted piperazines and homopiperazines (X) are commercially available and/or described in the chemical literature. A convenient synthesis for homopiperazines is shown for a specific intermediate compound in Scheme 5. The 2-oxazolidinone intermediate (XV) is ring-opened with HBr in glacial acetic acid and recyclized to intermediate (X) in refluxing n-BuOH.

Additional reaction intermediates and Formula (I) products can be prepared by appropriate modification of the foregoing synthetic schemes and procedures. Such modifications would be obvious to practitioners skilled in the chemical art. Additional examples and experimental procedures are provided infra.

The compounds of this invention demonstrate binding affinity at NPY Y$_1$ receptors. This pharmacologic activity is assayed in SK-N-MC (human neuroblastoma) cell membranes using iodine-125-labeled I-PYY as a radioligand. The compounds of this invention had good binding affinities as evidenced by IC$_{50}$ values being about 10 µM or less at NPY Y$_1$ receptors. Preferred compounds have IC$_{50}$ values less than 100 nM and most preferred compounds have IC$_{50}$ values of less than 10 nM. Although as a class, these types of dihydropyridines have significant affinity for $\alpha_1$-adrenergic receptors and/or Ca$^{++}$ channels, the compounds of this invention possess much weaker affinities for $\alpha_1$ adrenergic receptors and Ca$^{++}$ channels. As such, these compounds act as selective NPY antagonists at NPY Y$_1$ receptor sites. There is evidence that NPY contributes to certain symptoms in these disorders: hypertension, eating disorders, and depression/anxiety.[21] Compounds of this invention are expected to be useful in treating these disorders.

Selected compounds are tested further for their ability to block NPY-induced feeding in test animals by intraperitoneal administration to the animal prior to inducing feeding behavior with NPY. Taken together, these tests indicate that the compounds of this invention would be useful anorexiants and would function as anti-obesity agents with further use in various clinical eating disorders. Thus, another aspect of the invention concerns a process for reducing food intake in an obese mammal or a mammal with an eating disorder. The process comprises systemic administration to such a mammal of an anorexiant-effective dose of a Formula (I) compound or a pharmaceutically acceptable acid addition salt and/or hydrate thereof.

On the basis of pharmacologic testing, an effective dose given parenterally could be expected to be in a range of about 0.05 to 1 mg/kg body weight and if given orally would be expected to be in the range of about 1 to 20 mg/kg body weight.

For clinical applications, however, the dosage and dosage regimen must in each case be carefully adjusted, utilizing sound professional judgment and considering the age, weight and condition of the recipient, the route of administration and the nature and gravity of the illness. Generally, the compounds of the instant invention will be administered in the same manner as for available anorexiant drugs such as Diethylpropion, Mazindol, or Phentermine and the daily oral dose would comprise from about 70 to about 1400 mg, preferably 500 to 1000 mg administered from 1 to 3 times a day. In some instances, a sufficient therapeutic effect can be obtained at lower doses while in others, larger doses will be required.

The term systemic administration as used herein refers to oral, rectal, and parenteral (i.e. intramuscular, intravenous, and subcutaneous) routes. Generally, it will be found that when a compound of the present invention is administered orally, which is the preferred route, a larger quantity of reactive agent is required to produce the same effect as a smaller quantity given parenterally. In accordance with good clinical practice, it is preferred to administer the instant compounds at a concentration level that will produce effective anoretic effects without causing any harmful or untoward side effects. Similarly, the instant compounds can be administered to treat hypertension, depression and anxiety disorders.

Therapeutically, the instant compounds are generally given as pharmaceutical compositions comprised of an effective anorectic amount of a compound of Formula (I) or a pharmaceutically acceptable acid addition salt thereof and a pharmaceutically acceptable carrier. Pharmaceutical compositions for effecting such treatment will contain a major or minor amount, e.g. from 95 to 0.5% of at least one compound of the present invention in combination with the pharmaceutical carrier, the carrier comprising one or more solid, semi-solid, or liquid diluent, filler, and formulation adjuvant which is non-toxic, inert and pharmaceutically acceptable. Such pharmaceutical compositions are preferably in dosage unit forms; i.e., physically discrete units containing a predetermined amount of the drug corresponding to a fraction or multiple of the dose which is calculated to produce the desired therapeutic response. The dosage units can contain 1, 2, 3, 4, or more single doses, or, alternatively, one-half, one-third, or one-fourth of a single dose. A single dose preferably contains an amount sufficient to produce the desired therapeutic effect upon administration at one application of one or more dosage units according to the pre-determined dosage regimen usually a whole, half, third, or quarter of the daily dosage administered once, twice, three, or four times a day. Other therapeutic agents can also be present. Pharmaceutical compositions which provide from about 50 to 1000 mg of the active ingredient per unit dose are preferred and are conventionally prepared as tablets, lozenges, capsules, powders, aqueous or oily suspensions, syrups, elixirs, and aqueous solutions. Preferred oral compositions are in the form of tablets or capsules and may contain conventional excipients such as binding agents (e.g. syrup, acacia, gelatin, sorbitol, tragecanth, or polyvinylpyrrolidone), fillers (e.g. lactose, sugar, maize-starch, calcium phosphate, sorbitol, or glycine), lubricants (e.g. magnesium stearate, talc, polyethylene glycol or silica), disintegrants (e.g. starch) and wetting agents (e.g. sodium lauryl sulfate). Solutions or suspensions of a Formula (I) compound with conventional pharmaceutical vehicles are employed for parenteral compositions such as an aqueous solution for intravenous injection or an oily suspension for intramuscular injection. Such compositions having the desired clarity, stability and adaptability for parenteral use are obtained by dissolving from 0.1% to 10% by weight of the active compound in water or a vehicle consisting of a polyhydric aliphatic alcohol such as glycerine, propyleneglycol, and polyethelene glycols or mixtures thereof. The polyethyleneglycols consist of a mixture of non-volatile, usually liquid, polyethyleneglycols which are soluble in both water and organic liquids and which have molecular weights from about 200 to 1500.

DESCRIPTION OF THE SPECIFIC EMBODIMENTS

The compounds which constitute this invention and their methods of preparation will appear more fully from a consideration of the following examples which are given for the purpose of illustration only and are not to be construed as limiting the invention in sphere or scope. All temperatures are understood to be in degrees C when not specified.

The nuclear magnetic resonance (NMR) spectral characteristics refer to chemical shifts ($\delta$) expressed in parts per million (ppm) versus tetramethylsilane (TMS) as reference standard. The relative area reported for the various shifts in the proton NMR spectral data corresponds to the number of hydrogen atoms of a particular functional type in the molecule. The nature of the shifts as to multiplicity is reported as broad singlet (br s), singlet (s), multiplet (m), doublet (d), triplet (t) doublet of doublets (dd), quartet (q) or pentuplet (p). Abbreviations employed are DMSO-$d_6$, (deuterodimethylsulfoxide), $CDCl_3$ (deuterochloroform), and are otherwise conventional. The infrared (IR) spectral descriptions include only absorption wave numbers ($cm^{-1}$) having functional group identification value. The IR determinations were employed using potassium bromide (KBr) as diluent. The elemental analyses are reported as percent by weight.

A. Preparation of Intermediates
1. Formula (VII) Compounds

EXAMPLE 1

General Procedure for the Preparation of Knoevenagel Adducts (VII)

Following a general method reported by Jones[9], a mixture of 300 mmol each of 3-nitrobenzaldehyde and the requisite β-keto ester was dissolved in 250 mL of toluene and pipeddine (2.5 mL) and glacial HOAc (5 mL) were added. The solution was then allowed to reflux several hr during which time the theoretical amount of $H_2O$ was removed by a Dean-Stark trap. The toluene was then removed in vacuo and the resulting Knoevenagel products purified by flash chromatography ($SiO_2$: EtOAc/Hex) or crystallization.

EXAMPLE 2

3-(3-Nitrophenyl)-2-(1-oxobutyl)-2-propenoic acid, ethyl ester

The yellow oil was isolated as a mixture of E and Z isomers in 47% yield: $^1$H NMR ($CDCl_3$) δ8.23 (m, 2H), 7.52 (m, 3H), 4.32 (m, 2H), 2.67 and 2.53 (t, 2H, J=7.2 Hz), 1.66 (m, 2H), 1.29 (m, 2H), and 0.97 and 0.87 (t, 3H, J=7.4 Hz). Anal. Calcd for $C_{15}H_{17}NO_5$: C, 61.85; H, 5.88; N, 4.81. Found: C, 61.76; H, 5.86; N, 4.82.

EXAMPLE 3

2-(Dimethoxyacety)-3-(3-nitrophenyl-2-propenoic acid, ethyl ester

This adduct was isolated as an orange oil in 34% yield: $^1$H NMR ($CDCl_3$) δ8.34–8.23 (m, 2H), 7.99–7.70 (m, 4H), 4.94–4.93 (m, 1H), 4.30–4.22 (m, 1H), 3.79 (d, 1H, J=8 Hz), 3.35–3.33 (m, 6H), 1.28–1.13 (m, 3H). Anal. Calcd, for $C_{15}H_{17}NO_7$: C, 55.73; H, 5.30; N, 4.33. Found: C, 55.28; H, 4.84; N, 4.59.

2. Formula (V), (XII), and (XIII) Intermediates

EXAMPLE 4

General Method for the Preparation of Dihydropyridine Intermediates (V)

For the symmetrical dihydropyridines of Formula (V), the requisite β-keto ester (126 mmol), 3-nitrobenzaldehyde (63 mmol), and $NH_4OAc$ (95 mmol) were refluxed for several h in 150 mL of EtOH using standard Hantzsch conditions[8]. The crude reaction mixture was cooled to ambient temperature and the volatiles removed in vacuo. The symmetrical dihydropyridines were crystallized from EtOH. Generally, for the asymmetrical Formula (V) intermediate, a mixture of the requisite Knoevenagel adduct (VII) (70 mmol) and methyl 3-aminocrotonate (70 mmol) was refluxed in i-PrOH overnight (24 h). The volatiles were then removed in vacuo and the crude products recrystallized from EtOH.

EXAMPLE 5

1,4-Dihydro-2-methyl-4-(3-nitrophenyl)-6-propyl-3, 5-pyridinedicarboxylic acid, ethyl[5] methyl[3] ester The compound was obtained as a bright yellow solid in 34% yield; mp 102°–105° C.; $^1$H NMR ($CDCl_3$) δ8.09 (t, 1H, J=2 Hz), 7.99–7.96 (m, 1H), 7.63–7.59 (m, 1H), 7.35 (t, 1H, J=8 Hz), 5.77 (br s, 1H), 4.14–3.99 (m, 2H), 3.63 (s, 3H), 2.77–2.61 (m, 2H), 2.34 (s, 3H), 1.72–1.53 (m, 2H), 1.20 (t, 3H, J=7 Hz), 0.97 (t, 3H, J=7.4 Hz). Anal Calcd. for $C_{20}H_{23}N_2O_6 \cdot 0.2H_2O$: C, 61.43; H, 6.03; N, 7.16. Found: C, 61.52; H, 6.29; N, 7.10.

EXAMPLE 6

1,4-Dihydro-2-methyl-6-(dimethoxymethyl)-4-(3-nitrophenyl)-3,5-pyridinedicarboxylic acid, ethyl[5] methyl[3] ester (XIII)

The compound was obtained in 35% yield after purification by flash chromatography ($SiO_2$: EtOAc/Hex): mp 118°–122° C.; $^1$H NMR ($CDCl_3$) δ8.14 (t, 1H, J=2 Hz), 8.02–7.99 (m, 1H), 7.65–7.61 (m, 1H), 7.38 (t, 1H, J=8 Hz), 6.82 (br s, 1H), 6.03 (s, 1H), 5.13 (s, 1H), 4.17–4.06 (m, 2H), 3.64 (s, 3H), 3.48 (s, 3H), 3.43 (s, 3H), 2.38 (s, 3H), 1.24 (t, 3H, J=7 Hz); $^{13}$C NMR ($CDCl_3$) δ167.4, 166.0, 149.3, 148.3, 145.1, 143.9, 134.2, 128.8, 122.9, 121.5, 104.7, 102.5, 98.5, 60.4, 55.7, 55.1, 51.2, 40.0, 19.7, 14.1. Anal Calcd. for $C_{20}H_{24}N_2O_8$: C, 57.14; H, 5.75; N, 6.66. Found: C, 57.07; H, 5.64; N, 6.64.

EXAMPLE 7

1,4-Dihydro-2,6-dimethyl-4-(3-nitrophenyl)-3,5-pyridinedicarboxylic acid, n-butyl methyl ester A solution of n-butyl acetoacetate (0.10 mole), methyl 3-aminocrotonate (0.10 mole), 3-nitrobenzaldehyde (0.10 mole) and 150 mL of i-PrOH was refluxed overnight (18 h). The volatiles were removed in vacuo and the residue purified by flash chromatography (SiO2: EtOAc/Hex) to furnish the product in 49% yield as low melting, yellow solid: mp 69°–70° C.; 1H NMR (DMSO-$d_6$) $\delta$9.03 (s, 1H), 7.98 (m, 2H), 7.58 (m, 2H), 4.96 (s, 1H), 3.91 (m, 2H), 3,53 (s, 3H), 2.28 (s, 3H), 2.26 (s, 3H), 1.45 (p, 2H, J=6.6 Hz), 1.18 (m, 4H), and 0.83 (t, 3H, J=7.4 Hz); $^{13}$C NMR (DMSO-$d_6$) $\delta$167.0, 166.5, 150.1, 147.5, 146.5, 134.1, 129.7, 121.7, 121.1, 101.0, 100.9, 63.0, 50.8, 39.1, 30.2, 18.7, 18.3, and 13.5. Anal. Calcd for $C_{20}H_{24}N_2O_6$: C, 61.85; H, 6.23; N, 7.21. Found: C, 62.02; H, 6.21; N, 6.95.

EXAMPLE 8

2-Cyano-1,4-dihydro-6-methyl-4-(3-nitrophenyl)-3, 5-pyridinedicarboxylic acid, ethyl[3] methyl[5] ester The acetal intermediate of Example 6 (XIII) (24 mmol) was taken up in 80 mL of acetone and 6N HCl (8 mL) was added. After stirring at ambient temperature for 1.5 h, the solvent was removed in vacuo. The resulting solid was rinsed with one portion of $H_2O$ and then filtered. Purification by flash chromatography (SiO$_2$: EtOAc/Hex) furnished the formyl derivative (XII) in 88% yield as an orange solid: mp 111°–114° C.; $^1$H NMR (CDCl$_3$) $\delta$8.12–8.01 (m, 2H), 7.61–7.46 (m, 1H), 7.41 (t, 1H, J=8 Hz), 7.04 (br s, 1H), 5.23–5.22 (m, 1H), 4.30–4.14 (m, 2H), 3.77 (s, 1H), 3.64 (s, 3H), 2.43 (s, 3H), 1.28 (t, 3H, J=7 Hz); $^{13}$C NMR (CDCl$_3$) $\delta$186.5, 167.0, 165.2, 148.4, 147.6, 145.2, 139.0, 134.2, 129.3, 123.0, 122.1, 115.0, 101.9, 61.6, 52.4, 51.4, 40.7, 19.6, 14.1. Anal. Calcd. for $C_{18}H_{18}N_2O_7$: C, 57.75; H, 4.85; N, 7.48.Found: C, 57.61; H, 4.60; N, 7.33.

The formyl intermediate ((XII); 8.7 mmol) was dissolved in 25 mL glacial acetic acid and NH$_2$OH•HCl (9.6 mmol) and NaOAc (12 mmol) were added. The solution was stirred at room temperature for 2.5 h and then Ac$_2$O (29 mmol) was added and the reaction stirred for an 1.5 h at room temperature and at 94° C. for an additional 4 h. The excess HOAc and Ac$_2$O were removed in vacuo. Water was added to the residue and the aq layer was neutralized with aq NaHCO$_3$. The suspension was extracted with EtOAc and the combined organic fractions were washed once with H$_2$O, and then dried over MgSO$_4$. After filtration, the filtrate was concentrated in vacuo to give an oil which solidified on standing. The cyano derivative (V) was obtained in 40% yield as a yellow solid after trituration from EtOAc/Hex: mp 169°–170° C.; $^1$H NMR (CDCl$_3$) $\delta$8.14–8.01 (m, 2H), 7.63–7.60 (m, 1H), 7.47–7.38 (m, 1H), 7.13 (s, 1H), 5.19 (s, 1H), 4.27–4.09 (m, 2H), 3.65 (s, 3H), 2.41 (s, 3H), 1.29 (t, 3H, J=7 Hz); $^{13}$C NMR (CDCl$_3$) $\delta$166.7, 163.7, 148.7, 146.7, 145.5, 134.3, 129.4, 123.0, 122.4, 116.5, 113.1, 111.8, 102.1, 62.0, 52.0, 39.5, 19.2, 13.9.

EXAMPLE 9

1,4-Dihydro-2,6-dimethyl-4-(3-nitrophenyl)-5-(3-methyl-1,2,4-oxadiazol-5-yl)-3-pyridinecarboxylic acid, methyl ester The starting 1,4-dihydro-2,6-dimethyl-4-(3-nitrophenyl)-3,5-pyridinedicarboxylic acid, mono-methyl ester (XIV)[14] (11.1 mmol) was treated with carbonyl diimidazole (12 mmol) in 60 mL of MeCN. After stirring for 2 h, acetamidoxime•HCl (15.8 mmol), and Et$_3$N (22.2 mmol) were added. The resulting mixture was refluxed for 17 h under N$_2$ and the volatiles were then removed in vacuo. The residue was taken up in CH$_2$Cl$_2$ and washed with H$_2$O and brine, and dried over MgSO$_4$. After filtration, the volatiles were removed in vacuo to give a yellow foam. The crude intermediate O-acyl amidoxime was purified by flash chromatography (SiO$_2$: MeOH/EtOAc) to give 3.13 g (73%) of this intermediate. This material was then heated neat in a 200° C. oil bath for 20 min under a N$_2$ flow. The resulting dark residue was recrystallized from EtOAc/Hex to give the oxadiazole intermediate (V) in 37% yield as a yellow crystalline solid: mp 221°–222° C.; $^1$ H NMR (DMSO-$d_6$) $\delta$9.37 (s, 3H), 7.99 (m, 2H), 7.66 (m, 1H), 7.54 (t, 1H, J=7.9 Hz), 5.18 (s, 1H), 3.57 (s, 3H), 2.41 (s, 3H), 2.31 (s, 3H), and 2.23 (s, 3H); $^{13}$C NMR (DMSO-$d_6$) $\delta$175.5, 166.9, 166.5, 149.0, 148.0, 146.6, 144.4, 134.1, 130.0, 121.7, 100.7, 95.6, 51.1, 39.4, 18.5, 18.3, and 11.4. Anal. Calcd for $C_{18}H_{18}N_4O_5$: C, 58.37; H, 4.90; N, 15.13. Found: C, 58.56; H, 4.88; N, 14.88. Lit:[17] mp 239°–240° C.

3. Aniline Intermediates of Formula (IV)

EXAMPLE 10

General Reductive Procedures for the Conversion of the Nitroaryl Dihydropyridines (V) to the Anilines (IV)

Catalytic Hydrogenation Method A. To a N$_2$ solution of the nitro aromatic dihydropyridine (V) (10 mmol) in 80 mL of EtOH, was added 0.5–1.0 g of 5% Pt on sulfided carbon and the resulting suspension shaken on a Parr Hydrogenation apparatus at room temperature under 60 psi of H$_2$. After several h the reduction was usually complete as judged by theoretical H$_2$ consumption. The suspension was then filtered through Celite and the filtrate concentrated in vacuo to give the anilines (IV). These were then purified by recrystallization or flash chromatography in the indicated solvents. In some of the examples the crude aniline derivatives were conveded to a salt form and then recrystallized.

Iron Method B.[15] In a 250-mL three-necked flask equipped with mechanical stirrer and reflux condenser was added a solution of NH$_4$Cl (64 mmol) in 50 mL of H$_2$O. iron powder (38 mg-atom, 325 mesh) and a solution of the nitro aromatic dihydropyridine (V) (11 mmol) in 50 mL of MeOH. The resulting mixture was stirred at reflux for 6 h and then filtered through Celite and rinsed with copious amounts of MeOH. The filtrate was partially concentrated in vacuo to yield an aq suspension, which was extracted with CH$_2$Cl$_2$. The combined organic extracts were dried over Na$_2$SO$_4$, filtered, and the volatiles removed in vacuo to yield the crude anilines (IV). These were purified as above in the hydrogenation method.

Nickel/Borohydride Resin Method C. According to the general method of Yoon[11] the borohydride exchange resin (12 g) was suspended in 40 mL of MeOH and Ni(OAc)$_2$•4H$_2$O (0.60 mmol) was added. After stirring several min, the requisite nitro aromatic derivative (V) (6 mmol) was added and the resulting black mixture stirred overnight at room temperature. After filtration through a plug of Celite, the reaction solution was concentrated in vacuo to give the reduced aniline derivatives (IV).

EXAMPLE 11

4-(3-Aminophenyl)-1,4-dihydro-2-methyl-6-propyl-3,5-pyridinedicarboxylic acid, ethyl[5] methyl[3] ester, fumaric acid salt This compound was obtained as an orange-brown solid in 91% yield (Method B): mp 92°–95° C.; $^1$H NMR (MeOD) $\delta$7.30–7.17 (m, 3H), 7.02–6.99 (m, 1H), 6.26 (s, 2H), 4.06

(q, 2H, J=14 Hz), 3.61 (s, 3H), 2.78–2.52 (m, 2H), 2.30 (s, 3H), 1.69–1.55 (m, 2H), 1.21 (t, 3H, J=7 Hz), 0.97 (t, 3H, J=7.4 Hz); $^{13}$C NMR (MeOD) δ170.5, 169.9, 169.04, 151.9, 147.0, 135.0, 134.9, 130.5, 127.5, 122.0, 120.3, 103.2, 103.0, 60.9, 51.4, 40.8, 34.7, 23.4, 18.6, 14.7, 14.3. Anal. Calcd. for $C_{20}H_{26}N_2O_4 \cdot 1.0C_4H_4O_4 \cdot 1.0H_2O$: C, 58.53; H, 6.55; N, 5.69. Found: C, 58.86; H, 6.22; N, 5.68.

EXAMPLE 12

4-(3-Aminophenyl)-1,4-dihydro-2,6-dimethyl-3,5-pyridinedicarboxylic acid, ethyl methyl ester (Cf: reference 12a)

This compound was obtained in 92% yield as a grey solid after crystallization from EtOAc/Hex (Method A): mp 173°–175° C.

EXAMPLE 13

4-(3-Aminophenyl)-1,4-dihydro-2,6-dimethyl-3,5-pyridinedicarboxylic acid, diethyl ester hydrochloride salt (Cf: reference 12a)

The compound was isolated in 82% yield (Method A) after purification by flash chromatography (SiO$_2$: EtOAc/Hex). A small portion of the aniline was converted to the HCl salt by treatment with ethereal HCl. After trituration from Et$_2$O, the compound was obtained as a pale yellow solid: mp 212°–213° C.

EXAMPLE 14

4-(3-Aminophenyl)-1,4-dihydro-2,6-dimethyl-3,5-pyridinedicarboxylic acid, dimethyl ester (Cf: reference 12a)

The compound was obtained in 58% yield as a colorless solid after crystallization from EtOH (Method A): mp 214°–215° C.

EXAMPLE 15

4-(3-Aminophenyl)-1,4-dihydro-2,6-dimethyl-3,5-pyridinedicarboxylic acid, n-butyl methyl ester hydrochloride salt The compound was isolated as a yellow oil in 68% yield (Method A) after flash chromatography (SiO$_2$: EtOAc/Hex). A small portion of the oil was converted to the HCl salt by treatment with ethereal HCl: Mp 135°–145° C.; $^1$H NMR (DMSO-d$_6$) δ10.20 (br s, 2H), 9.12 (s, 1H), 7.29 (t, 1H, J=7.8 Hz), 7.12 (m, 3H), 4.89 (s, 1H), 3.94 (m, 2H), 3.54 (s, 3H), 2.27 (s, 3H), 2.26 (s, 3H), 1.49 (m, 2H), 1.22 (m, 2H), and 0.89 (t, 3H, J=8.0 Hz); $^{13}$C NMR (DMSO-d$_6$) δ167.2, 166.8, 149.7, 146.1, 132.1, 129.1, 125.4, 121.7, 120.6, 101.1, 101.0, 62.9, 50.7, 38.6, 30.3, 18.7, 18.3, and 15.6. Anal. Calcd for $C_{20}H_{26}N_2O_4 \cdot HCl \cdot 0.50H_2O$: C, 59.48; H, 6.99; N, 6.94. Found: C, 59.52; H, 6.82; N, 3.58.

EXAMPLE 16

4-(3-Aminophenyl)-1,4-dihydro-2,6-dimethyl-3,5-pyridinedicarboxylic acid, 1,1-dimethylethyl methyl ester The aniline was obtained in 87% yield as a yellow solid after purification by flash chromatography (SiO$_2$: EtOAc/Hex): mp 85°–90° C.; $^1$H NMR (CDCl$_3$) δ6.97 (t, 1H, J=7.7 Hz), 6.66 (d, 1H, J=7.7 Hz), 6.58 (s, 1H), 6.44 (d, 1H, J=7.8 Hz), 5.53 (br s, 1H), 4.86 (s, 1H), 3.62 (s, 3H) 2.29 (s, 3H), 2.26 (s, 3H), and 1.39 (s, 9H); $^{13}$C NMR (CDCl$_3$) δ168.2, 167.1, 148.7, 145.9, 144.1, 142.5, 128.6, 118.5, 114.9, 113.1, 103.4, 79.8, 50.9, 39.6, 28.3, 19.7, and 19.6. Anal. Calcd for $C_{20}H_{26}N_2O_4$: C, 67.02; H, 7.32; N, 7.82. Found: C, 66.97; H, 7.43; N, 7.68.

EXAMPLE 17

4-(3-Aminophenyl)-1,4-dihydro-2-cyano-6-methyl-3,5-pyridine-dicarboxylic acid, ethyl[3] methyl[5] ester This material was prepared using the general Fe/NH$_4$Cl procedure described above for anilines (Method B). Aniline (IV) was obtained in 69% yield as a yellow solid: mp 181°–182° C.; $^1$H NMR (CDCl$_3$) δ8.73 (s, 1H), 6.96 (t, 1H, J=8 Hz), 6.60–6.44 (m, 3H), 4.92 (s, 1H), 4.25–4.08 (m, 2H), 3.70 (s, 1H), 3.58 (s, 3H), 2.30 (s, 3H), 1.23 (t, 3H, J=7 Hz); $^{13}$C NMR (CDCl$_3$) δ167.5, 164.5, 146.4, 145.6, 129.2, 118.3, 118.1, 117.7, 116.6, 114.7, 114.0, 101.8, 61.3, 51.2, 39.1, 18.7, 14.0. Anal. Calcd. for $C_{18}H_{19}N_3O_4$: C, 61.94; H, 5.47; N, 11.53. Found: C, 1.51; H, 5.34; N, 11.75.

EXAMPLE 18

4-(3-Aminophenyl)-1,4-dihydro-2,6-dimethyl-5-(3-methyl-1,2,4-oxadiazol-5-yl)-3-pyridinecarboxylic acid, methyl ester This compound was prepared using the iron procedure (Method B). The aniline derivative was obtained in quantitative yield as a yellow solid: mp 248°–249° C.; $^1$H NMR (DMSO-d$_6$) δ9.08 (s, 1H), 6.80 (t, 1H, J=7.7 Hz), 6.39 (s, 1H), 6.34 (d, 1H, J=7.7 Hz), 6.27 (d, 1H, J=7.7 Hz), 4.93 (s, 1H), 4.88 (br s, 2H), 3.58 (s, 3H), 2.38 (s, 3H), 2.25 (s, 3H), and 2.23 (s, 3H); $^{13}$C NMR (DMSO-d$_6$) δ175.9, 167.2, 166.2, 148.4, 147.4, 144.9, 143.3, 128.5, 114.7, 112.7, 112.0, 101.5, 96.0, 50.7, 39.0, 18.2, and 11.2. HRMS. Calcd for $C_{18}H_{21}N_4O_3$ (M+H): 341.1614. Found: 341.1606.

EXAMPLE 19

4-(3-Aminophenyl)-5-cyano-1,4-dihydro-2,6-dimethyl-3-pyridinecarboxylic acid, methyl ester This compound was prepared using the iron procedure (Method B). The aniline was obtained in 10% yield as a tan solid after recrystallization from EtOH: mp 234°–235° C.; $^1$H NMR (DMSO-d$_6$) δ9.09 (br s, 1H), 6.90 (t, 1H, J=7.5 Hz), 6.36 (m, 2H), 6.30 (d, 1H, J=7.5 Hz), 5.01 (br s, 2H), 4.27 (s, 1H), 3.48 (s, 3H), 2.24 (s, 3H), and 1.99 (s, 3H); $^{13}$C NMR (DMSO-d$_6$) δ167.2, 148.7, 146.8, 146.0, 145.2, 128.9, 120.2, 114.6, 112.5, 99.7, 84.5, 50.7, 40.6, 18.4, and 17.5. Anal. Calcd for $C_{16}H_{17}N_3O_2 \cdot 0.22H_2O$: C, 66.91; H, 6.12; N, 14.63. Found: C, 66.91; H, 6.07; N, 14.40.

EXAMPLE 20

4-(3-Amino-4-chlorophenyl)-1,4-dihydro-2,6-dimethyl-3,5-pyridine-dicarboxylic acid, ethyl methyl ester This dihydropyridine was obtained using the iron reduction procedure (Method B). It was isolated in 99% yield as light yellow solid: mp 68°–90° C.; $^1$H NMR (CDCl$_3$) δ7.03 (d, 1H), 6.62 (m, 2H), 5.68 (br s, 1H), 4.88 (s, 1H), 4.08 (m, 2H), 3.89 (br s, 2H), 3.63 (s, 3H), 2.29 (s, 6H), and 1.21 (t, 3H). Anal. Calcd. for $C_{18}H_{21}N_2O_4Cl$: C, 59.26; H, 5.80; N, 7.68. Found: C, 59.04; H, 5.79; N, 7.56.

EXAMPLE 21

4-[3-Amino-4-(2-propenyloxyphenyl)]-1,4-dihydro-2,6-dimethyl-3,5-pyridinedicarboxylic acid dimethyl ester To a suspension of hexane-washed NaH (17 mmol, 60% in mineral oil) in 5 mL of DMF was added a solution of compound (V), $R^5$=OH (14.1 mmol) in 50 mL of DMF. The resulting dark red solution was stirred at room temperature for 10 min and then allyl bromide (22 mmol) was introduced. After the reaction was stirred an additional 21 h, it was poured into 300 mL of $H_2O$ and extracted with $CH_2Cl_2$. The combined organic portions were washed with $H_2O$ and brine and then dried over $MgSO_4$. Filtration and removal of the volatiles in vacuo afforded compound (V), R=allyloxy as an oil which was used without further purification and was subsequently subjected to the iron reduction method (Method B). The resulting aniline compound (IV), R-allyloxy was obtained in 50% yield after purification by flash chromatography ($SiO_2$: EtOAc/Hex) and was isolated as a pale yellow solid: 155°–157° C.; $^1$H NMR (DMSO-$d_6$) δ8.74 (br s, 1H), 6.58 (d, 1H, J=8.3 Hz), 6.44 (d, 1H, J=2.1 Hz), 6.26 (d of d, 1H, J's=8.3 and 2.1 Hz), 6.01 (m, 1H), 5.40 (d, 1H), 5.19 (d, 1H), 4.74 (s, 1H), 4.55 (br s, 2H), 4.32 (m, 2H), 3.54 (s, 6H), and 2.22 (s, 6H); $^{13}$C NMR (DMSO-$d_6$) δ167.7, 145.0, 143.7, 140.6, 137.2, 134.4, 116.7, 114.7, 113.2, 111.7, 101.8, 68.5, 50.6, 37.6, and 18.2. Anal. Calcd for $C_{20}H_{24}N_2O_5$: C, 64.50; H, 6.50; N, 7.52. Found: C, 64.32; H, 6.59; N, 7.35.

EXAMPLE 22

General Procedure for Preparation of Formula (III) Anilide Intermediates

To a solution of an appropriate Formula (IV) aniline intermediate (2.5 mmole) in THF (50 mL) at 0° is added a chloroacyl chloride (2.5 mmole) also in THF (15 mL). The reaction is stirred at 0° for 0.5 to 1 hour and then at room temperature for 0.5 to 1 hour until judged complete. Volatiles are removed in vacuo and the residue is purified, generally by flash silica gel chromatography.

EXAMPLE 23

1,4-Dihydro-4-[3-[[3-chloro-1-oxo-1-propyl]amino]phenyl]-2,6-dimethyl-3,5-pyridinedicarboxylic acid, dimethyl ester 4-(3-Aminophenyl)-1,4-dihydro-2,6-dimethyl-3,5-pyridinedicarboxylic acid, dimethyl ester (0.8 g, 2.53 mmol) was dissolved in THF (50 mL) and cooled to 0° C. 3-Chloropropionyl chloride (0.32 g, 2.53 mmol) was dissolved in THF (15 mL) and added dropwise to the mixture over 10 min. The mixture was stirred at 0° C. for 1 h., concentrated in vacuo, and the residue extracted with $CH_2Cl_2$/brine. The $CH_2Cl_2$ layer was dried over $Na_2SO_4$, filtered, and concentrated in vacuo. Silica gel chromatography (1:1 to 1:0 EtOAc:hexane gradient) gave the title compound (1.05 g, 100%) as a pale yellow foam.

EXAMPLE 24

1,4-Dihydro-4-[3-[[4-chloro-1-oxo-1-butyl]amino]phenyl]-2,6-dimethyl-3,5-pyridinedicarboxylic acid, dimethyl ester 4-(3-Aminophenyl)-1,4-dihydro-2,6-dimethyl-3,5-pyridinedicarboxylic acid, dimethyl ester (1.0 g, 3.16 mmol) was dissolved in THF (50 mL) and cooled to 0° C. 4-Chlorobutyryl chloride (0.446 g, 3.16 mmol) was dissolved in THF (10 mL) and added dropwise to the mixture over 5 min. The mixture was stirred at 0° C. for 0.5 h. and then at 23° C. for 1 h. The solvent was removed in vacuo and the concentrate chromatographed over silica gel (1:4 to 1:0 EtOAc:hexane gradient) to give the title compound (1.33 g, 100%) as a pale yellow foam.

EXAMPLE 25

1,4-Dihydro-4-[3-[[5-chloro-1-oxo-1-pentyl]amino]phenyl]-2,6-dimethyl-3,5-pyridinedicarboxylic acid, dimethyl ester 4-(3-Aminophenyl)-1,4-dihydro-2,6-dimethyl-3,5-pyridinedicarboxylic acid, dimethyl ester (2.3 g, 7.28 mmol) was dissolved in THF (50 mL) and cooled to 0° C. 5-Chlorovaleryl chloride (1.13 g, 7.28 mmol) was dissolved in THF (15 mL) and added dropwise to the mixture over 15 min. The mixture was stirred at 0° C. for 1 h., the solvent removed in vacuo, and the residue was extracted using $CH_2Cl_2$/water. The $CH_2Cl_2$ layer was dried over $Na_2SO_4$, filtered, and concentrated in vacuo. Silica gel chromatography (1:1 to 1:0 EtOAc:hexane gradient) of the concentrate gave the title compound (3.16 g, 100%) as a pale yellow foam.

4. Intermediates of Formula (II)

EXAMPLE 26

General Chloroalkyl Isocyanate Procedure for Preparation of Formula (II) Urea Intermediates To a solution of the appropriate Formula (IV) aniline intermediate (6 mmol) in $CH_2Cl_2$ (30 mL) under $N_2$ is added the chloroalkyl isocyanate (7 mmol). The reaction is stirred at room temperature or at reflux until judged complete by TLC analysis (2–24 hr). The reaction solution is washed with $H_2O$ and brine and then dried ($MgSO_4$). After filtration, the volatiles are removed in vacuo and the residue is generally taken up in MeCN (35 mL) and immediately carried on with reaction with a selected piperazine or homopiperazine reactant of Formula (X).

EXAMPLE 27

Preparation of Formula (XXXIV) Isocyanate Intermediates a) 1,4-Dihydro-4-[3-[(methoxycarbonyl)amino]phenyl]-2,6-dimethyl-3,5-pyridinedicarboxylic acid, dimethyl ester (XXIV).

A solution of 1,4-dihydro-4-(3-aminophenyl)-2,6-dimethyl-3,5-pyridinedicarboxylic acid, dimethyl ester (IV: 63.2 g, 200 mmol) and pyridine (18 mL, 220 mmol) in $CH_2Cl_2$: MeCN 1:1 (1.5 L) was cooled to 0° C. A solution of methyl chloroformate (16 mL, 210 mmol) in $CH_2Cl_2$ (50 mL) was added dropwise over 10 min. Stirring was continued at 0° C. for 30 min, then the reaction was warmed to room temperature and stirred for an additional hour. The reaction mixture was washed with saturated $Na_2CO_3$ (500 mL) and rinsed with $H_2O$ (2×500 mL). The organic extract was filtered to afford a white solid (37.1 g). The filtrate was then dried ($Na_2SO_4$), and the solvent was removed in vacuo. The residue was suspended in a minimum of EtOAc and filtered. The resulting solid was rinsed with a small amount of EtOAc, followed by $Et_2O$ to give an additional 30.8 g. Both crops were combined for a yield of 67.9 g (91%): mp 215°–218° C.; 1H NMR (DMSO-$d_6$) d 9.51 (s, 1H), 8.88 (s, 1H), 7.28 (s, 1H), 7.22 (d, 1H, J=8.1 Hz), 7.08 (t, 1H, J=7.8 Hz), 6.74 (d, 1H, J=7.8 Hz), 4.85 (s, 1H), 3.62 (s, 3H), 3.54 (s, 6H), 2.24 (s, 6H); $^{13}$C NMR (DMSO-$d_6$) δ167.4, 153.9, 148.2, 145.8, 138.9, 128.3, 121.0, 117.1, 115.9, 101.3, 51.5, 50.6, 38.4, 18.2; Anal Calcd for $C_{19}H_{22}N_2O_6$•0.1 $H_2O$: C, 60.66; H, 5.95; N, 7.45. Found: C, 60.50; H, 5.85; N, 7.55.

b) 1,4-Dihydro-4-(3-isocyanatophenyl)-2,6-dimethyl-3,5-pyridinedicarboxylic acid, dimethyl ester (XXXIV).

According to the general procedure described by Valli and Alper,[22] a solution of the carbamate (XXIV) (15.2 g, 40.6 mmol) and Et$_3$N (8.4 mL, 60 mmol) in anhydrous THF (300 mL) was refluxed under N$_2$ for 5 min, and then allowed to cool for 10 min. Chlorocatecholborane (8.78 g, 57 mmol) was added, and the resulting mixture was refluxed under N$_2$ for 5 min. The solvent was then removed in vacuo, and the residue was taken up in CH$_2$Cl$_2$ (300 mL). The resulting solution was washed with 1N aqueous HCl (150 mL), followed by 1N aqueous NaOH (150 mL). The organic extract was dried (Na$_2$SO$_4$) and the solvent was removed in vacuo to furnish a cream solid (13.9 g, quantitative yield): mp 170°–173° C.; $^1$H NMR (CDCl$_3$) d 7.11 (m, 2H), 6.96 (s, 1H), 6.86 (d, 1H, J=7.5 Hz), 5.74 (s, 1H), 4.97 (s, 1H), 3.65 (s, 6H), 2.34 (s, 6H); $^{13}$C NMR (CDCl$_3$) d 167.8, 149.2, 144.4, 133.0, 129.0, 125.3, 124.0, 122.7, 103.5, 51.1, 39.3, 19.6; IR (KBr): 2272 cm$^{-1}$; Anal. Calcd for C$_{18}$H$_{18}$N$_2$O$_5$: C, 63.15; H, 5.30; N, 8.18. Found: C, 63.17; H, 5.33; N, 7.98.

5. Intermediates of Formula (X)

EXAMPLE 28

1-(2-methoxyphenyl)homopiperazine a) 3-(3-Chloropropyl)-2-oxazolidinone (XVI).

To a mechanically stirred, room temperature suspension of NaH (0.305 mole, hexane washed) in 50 mL of DMF under N$_2$, was added 2-oxazolidinone (0.287 mole) portion wise. After stirring the resulting gelatinous mixture overnight, 1,3-dichloropropane (0.643 mole) was added and the mixture stirred 4 days at room temperature. The volatiles were then removed in vacuo and the resulting white residue taken up in CH$_2$Cl$_2$ and washed with H$_2$O and brine, and dried over MgSO$_4$. After filtration, the material was passed through a short column (SiO$_2$: EtOAc/Hex) to give (XVI) as a clear oil in 95% yield: 1H NMR (CDCl$_3$) δ4.22 (t, 2H, J=6.6 Hz), 3.47 (m, 4H), 3.24 (t, 2H, J=7.0 Hz), and 1.98 (p, 2H, J=6.5 Hz); 13C NMR (CDCl$_3$) δ158.5, 61.8, 45.0, 42.0, 41.8, and 30.2. Anal. Calcd for C$_6$H$_{10}$ClNO$_2$: C, 44.05; H, 6.16; N, 8.56. Found: 41.17; H, 5.77; N, 8.26.

b) 3-[3-[(2-Methoxyphenyl)amino]propyl]-2-oxazolidinone, oxalic acid salt (XV).

A solution of (XVI) (40.1 mmol), o-anisidine (102 mmol), and 150 mg of NaI in 100 mL of dry MeCN was refluxed under N$_2$ 3 days. The solution was poured into 200 mL of H$_2$O and extracted with CH$_2$Cl$_2$. The combined organic extracts were washed with H$_2$O and brine and dried over MgSO$_4$. After filtration, the volatiles were removed in vacuo to yield a brown oil. Purification of the oil by flash chromatography (SiO$_2$: EtOAc/Hex) afforded (XV) as a clear oil in 66% yield. For analytical purposes, a small portion of the oil was converted to the oxalic acid salt. The salt was isolated as a colorless white solid after recrystallization from MeCN: mp 96°–97° C.; $^1$H NMR (DMSO-d$_6$) δ6.77 (m, 2H), 6.54 (m, 2H), 4.22 (t, 2H), 3.75 (s, 3H), 3.50 (t, 2H), 3.20 (t 2H, J=7.0 Hz), 3.06 (t, 2H, J=6.8 Hz), and 1.75 (p, 2H, J=6.9 Hz); $^{13}$C NMR (DMSO-d$_6$) δ161.1, 158.0, 146.6, 137.7, 121.1, 115.8, 109.9, 109.4, 61.6, 55.3, 44.0, 41.5, 40.3, and 26.3. Anal. Calcd for C$_{13}$H$_{18}$N$_2$O$_3$•C$_2$H$_2$O$_4$: C, 52.94; H, 5.92; N, 8.23. Found: C, 52.87; H, 6.02; N, 8.14.

c) Hexahydro-1-(2-methoxyphenyl)-1H-1,4-diazepine, hydrobromide salt (X). In a similar fashion to that described for intermediate piperazine preparation[18], (XV) (32.0 mmol) was taken up in 35 mL of 30% HBr in glacial HOAc and stirred 5 days at room temperature. After addition of 200 mL CH$_2$Cl$_2$, the white solid was collected by filtration and then taken up in 75 mL of n-BuOH and refluxed 12 days. After cooling to room temperature, Et$_2$O was added to precipitate a solid. The solid was collected by filtration and recrystallized from aq EtOH to give (X) as a colorless solid in 37% yield: mp 155°–157° C.; $^1$H NMR (DMSO-d$_6$) δ8.71 (br s, 2H), 6.87 (m, 4H), 3.78 (s, 3H), 3.29 (m, 4H), 3.20 (m, 4H), and 2.08 (m, 2H); $^{13}$C NMR (DMSO-d$_6$) δ151.4, 141.2, 122.0, 120.7, 118.1, 112.0, 55.5, 50.1, 49.3, 46.7, 44.0, and 25.2. Anal. Calcd for C$_{12}$H$_{18}$N$_2$O•1.3HBr: C, 45.91; H, 6.21; N, 8.93. Found: C, 45.99; H, 6.08; N, 8.81. Lit[16]: no data.

B. Synthesis of Formula (I) Products

1. B is a Covalent Bond

EXAMPLE 29

1,4-Dihydro-4-[3-[[5-[4-(7-methoxynaphthalen-1-yl)-piperazin-1-yl]-1-oxo-1-pentyl]amino]phenyl]-2,6-dimethyl-3,5-pyridinedicarboxylic acid, dimethyl ester 1,4-Dihydro-4-[3-[[5-chloro-1-oxo-1-pentyl]amino]phenyl]-2,6dimethyl-3,5-pyridinedicarboxylic acid, dimethyl ester (1.2 g, 2.76 mmol), 4-(7-methoxynaphthalen-1-yl)piperazine (1.2 eq., 0.8 g, 3.3 mmol), micropulverized potassium carbonate (1.0 g) and KI (1.0 g) were refluxed in CH$_3$CN (50 mL) for 24 h. The solvent was removed in vacuo and the residue was extracted using CH$_2$Cl$_2$/brine. The CH$_2$Cl$_2$ layer was dried over Na$_2$SO$_4$ and evaporated to give the crude product. Chromatography over silica gel (5–20% MeOH-EtOAc as eluent) gave the free base (460 mg, 26%) as a viscous oil. The purified product was dissolved in MeOH and 2 eq. of fumaric acid dissolved in MeOH was added. Upon addition of EtOAc and standing in the freezer, a precipitate formed which was filtered and washed with EtOAc to yield 297 mg (54%) of the fumarate salt, mp 160°–163° C.: IR (KBr) 1688, 1626, 1598, 1434, 1264, 1214 cm$^{-1}$; $^1$H NMR (300 MHz, DMSO-d$_6$) δ1.45–1.65 (br, 4H), 2.25 (s, 6H), 2.30 (t, J=6.7 Hz, 2H), 2.48 (m, 2H), 2.59 (t, J=4.7 Hz, 4H), 3.50 (5, J-4.4 Hz, 4H), 3.54 (s, 6H), 4.86 (s, 1H), 6.59 (s, 4H), 6.61 (m, 1H), 6.77–6.83 (m, 2H), 7.09 (t, J=7.8 Hz, 1H), 7.34 (s, 1H), 7.43 (d, J=8.8 Hz, 1H), 7.52 (m, 1H), 8.10 (m, 1H), 8.89 (s, 1H), 9.77 (s, 1H); MS (Ion spray) m/e 641 (MH+). Anal. Calcd. for C$_{37}$H$_{44}$N$_4$O$_6$•1.1 C$_4$H$_4$O$_4$: C, 64.71; H, 6.35; N, 7.29. Found: C, 64.59; H, 6.54; N, 7.29.

2. B is NH

EXAMPLE 30

General Procedure from Formula (II) Intermediates (Generated In Situ)

To a solution of the requisite aniline (IV) (6 mmol) under N$_2$ in 30 mL of CH$_2$Cl$_2$, was added 7 mmol of 3-chloropropyl isocyanate. The reaction was then stirred at room temperature or at reflux until judged complete by TLC analysis (2–24 h). The solution was washed with H$_2$O and brine and then dried over MgSO$_4$. After filtration, the volatiles were removed in vacuo and the residue was taken up in 35 mL of MeCN. To this solution was added the appropriate Formula (X) piperazine (10 mmol), micropulverized K$_2$CO$_3$ (7 mmol), and a catalytic amount of NaI (10 mg). The resulting suspension was allowed to reflux overnight under N$_2$ and then poured into 100 mL of H$_2$O. After extraction with CH$_2$Cl$_2$, the combined organic fractions were washed with H$_2$O and brine, and dried over MgSO$_4$. The suspension was filtered and the filtrate concentrated in vacuo to furnish the crude products of Formula (I). These were then purified by flash chromatography (SiO$_2$: ammoniated EtOAc/MeOH) and a salt generally prepared from the free base.

EXAMPLE 31

1,4-Dihydro-4-[3-[[[[3-[4-(2-methoxyphenyl)-1-piperazinyl]propyl]-amino]carbonyl]amino]phenyl]-2-methyl-6-propyl-3,5-pyridinedicarboxylic acid, ethyl[5] methyl[3] ester, hydrochloride salt This compound was obtained as an orange-brown solid in 70% yield: mp 168°–171° C. $^1$H NMR (DMSO-d$_6$) δ10.58 (br s, 1H), 8.85 (s, 1H), 8.69 (s, 1H), 7.11–6.91 (m, 6H), 6.68 (d, 1H, J=7.4 Hz), 6.50 (br s, 1H), 4.84 (s, 1H), 4.02–0.01 (m, 2H), 3.79 (s, 3H), 3.65–3.17 (m, 11H), 3.09–3.02 (m, 5H), 2.66–2.51 (m, 2H), 2.27 (s, 3H), 1.91 (br s, 2H), 1.57–1.50 (m, 2H), 1.16 (t, 3H, J=7 Hz), 0.9 (t, 3H, J=7.2 Hz); $^{13}$C NMR (DMSO-d$_6$) δ167.5, 166.8, 151.8, 149.4, 148.4, 145.8, 140.1, 139.4, 128.1, 123.5, 120.9, 120.0, 118.3, 116.7, 115.5, 112.0, 101.5, 101.1, 59.1, 55.4, 53.6, 51.2, 50.6, 46.9, 45.6, 36.4, 32.8, 24.5, 21.9, 18.2, 14.2, 13.8. Anal. Calcd. for $C_{35}H_{47}N_5O_6$•4HCl•1.0H$_2$O: C, 52.70; H, 6.70; N, 8.78. Found: C; 52.56; H, 6.43; N, 8.60. HRMS. Calcd for $C_{35}H_{47}N_5O_6$Na (M+Na): 656.3424. Found: 656.3436.

EXAMPLE 32

2-Cyano-1,4-dihydro-4-[3-[[[[3-[4-(2-methoxyphenyl)-1-piperazinyl]-propyl]amino]carbonyl]amino]phenyl]-6-methyl-3,5-pyridinedicarboxylic acid, ethyl[3] methyl[5] ester This material was prepared using the general 3-chloropropyl isocyanate/arylpiperazine method described supra. The product was obtained as an orange solid in 66% yield: mp 118°–122° C. $^1$H NMR (MeOD) δ7.23–7.10 (m, 3H), 7.02–6.83 (m, 5H), 5.01 (s, 1H), 4.21–4.16 (m, 2H), 3.84 (s, 3H), 3.62 (s, 3H), 3.05 (br s, 4H), 2.67 (br s, 4H), 2.53–2.47 (m, 2H), 2.34 (s, 3H), 1.81–1.72 (m, 2H), 1.26 (t, 3H, J=7 Hz). Anal. Calcd. for $C_{33}H_{40}N_6O_6$•2H$_2$O: C, 60.72; H, 6.79; N, 12.88. Found: C, 60.44; H, 6.73; N, 12.62.

EXAMPLE 33

1,4-Dihydro-4-[3-[[[[3-[4-(2-methoxyphenyl)-1-piperazinyl]propyl]-amino]carbonyl]amino]phenyl]-2,6-dimethyl-3,5-pyridinedicarboxylic acid, ethyl methyl ester hydrochloride salt The compound was isolated in 50% yield as a white solid after conversion to the HCl salt: mp 120° C. (dec); 1H NMR (DMSO-d$_6$) δ10.77 (br s, 1H), 8.94 (s, 1H0, 8.77 (s, 1H), 7.29 (d, 1H, J=9.1 Hz), 7.12 (s, 1H), 6.98 (M, 5H), 6.69 (d, 1H, J=7.7 Hz), 5.06 (br s, 4H), 4.84 (s, 1H), 3.80 (s, 3H), 3.56 (s, 3H), 3.49 (m, 4H), 3.13 (m, 8H), 2.27 (s, 3H), 2.26 (s, 3H), 2.04 (m, 2H), and 1.16 (t, 3H, J=7.8 Hz); $^{13}$C NMR (DMSO-d$_6$) δ167.5, 167.0, 155.5, 151.8, 148.3, 145.6, 145.3, 140.2, 139.2, 128.1, 123.6, 120.9, 120.0, 118.3, 116.6, 115.4, 112.0, 101.7, 101.3, 59.0, 55.4, 53.5, 51.1, 50.6, 46.9, 36.4, 24.4, 18.2, and 14.3. Anal. Calcd for $C_{33}H_{43}N_5O_6$•2HCl•1.0 H$_2$O: C, 56.89; H, 6.80; N, 10.05. Found: C, 57.01; H, 6.49; N, 10.08.

EXAMPLE 34

1,4-Dihydro-4-[3-[[[[3-[4-(2-methoxyphenyl)-1-piperazinyl]propyl]-amino]carbonyl]amino]phenyl]-2,6-dimethyl-3,5-pyridinedicarboxylic acid, diethyl ester hydrochloride salt This compound was purified by flash chromatography and then converted to the HCl salt and isolated as a creamy white solid in 78% yield after recrystallization from EtOH/MeCN: mp 164°–165° C.; $^1$H NMR (DMSO-d$_6$) δ10.75 (br s, 1H), 8.89 (s, 1H), 8.72 (s, 1H), 7.28 (d, 1H, J=8.1 Hz), 7.10 (s, 1H), 6.93 (m, 5H), 6.68 (d, 1H, J=-7.6 Hz), 6.23 (br s, 2H), 4.81 (s, 1H), 3.98 (m, 4H), 3.78 (s, 3H), 3.50 (m, 4H), 3.11 (m, 8H 2.24 (s, 6H), 1.89 (m, 2H), and 1.14 (m, 6H); $^{13}$C NMR (DMSO-d$_6$) δ167.1, 155.5, 151.8, 148.5, 145.2, 140.1, 139.3, 128.0, 123.6, 120.9, 120.3, 118.3, 116.8, 115.4, 112.0, 101.7, 59.0, 55.4, 53.6, 51.1, 46.9, 6.4, 24.5, 18.3, and 14.3. Anal. Calcd for $C_{34}H_{45}N_5O_6$•2HCl: C, 8.96; H, 6.84; N, 10.12. Found: C, 58.60; H, 6.63; N, 10.16.

EXAMPLE 35

1,4-Dihydro-4-[3-[[[[3-[4-(2-methoxyphenyl)-1-piperazinyl]propyl]-amino]carbonyl]amino]phenyl]-2,6-dimethyl-3,5-pyridinedicarboxylic acid, dimethyl ester hydrochloride salt This dihydropyridine was obtained in 55% yield after flash chromatography. It was converted to the HCl salt, recrystallized from MeOH/MeCN/Et$_2$O and obtained as a colorless white solid: mp 201°–202° C.; $^1$H NMR (DMSO-d$_6$) δ10.66 (br s, 1H), 8.95 (s, 1H), 8.75 (s, 1H), 7.27 (d, 1H, J=8.1 Hz), 7.09 (s, 1H), 6.93 (m, 5H), 6.65 (d, 1H, J=7.7 Hz), 5.67 (br s, 1H), 4.83 (s, 1H), 3.78 (s, 3H), 3.55 (s, 6H), 3.46 (m, 4H), 3.13 (m, 8H), 2.25 (s, 6H), and 1.89 (m, 2H); $^{13}$C NMR (DMSO-d$_6$) δ167.5, 155.5, 151.8, 148.1, 145.7, 142.7, 140.3, 139.3, 128.2, 123.6, 120.9, 119.8, 118.3, 116.5, 115.4, 112.0, 101.3, 55.4, 53.5, 51.2, 50.7, 46.9, 36.4, 24.5, and 18.2. Anal. Calcd for $C_{32}H_{41}N_5O_5$•2HCl: C, 57.84; H, 6.53; N, 10.54. Found: C, 57.82; H, 6.53; N, 10.43.

EXAMPLE 36

1,4-Dihydro-4-[3-[[[[3-[4-(2-methoxyphenyl)-1-piperazinyl]propyl]-amino]carbonyl]amino]phenyl]-2,6-dimethyl-3,5-pyridinedicarboxylic acid, n-butyl methyl ester hydrochloride salt This compound was obtained as a colorless white solid in 90% yield after recrystallization from MeCN/Et$_2$O: mp 165°–168° C.; $^1$H NMR (DMSO-d$_6$) δ10.84 (br s, 1H), 8.93 (s, 1H), 8.74 (s, 1H), 7.28 (d, 1H, J=8.0 Hz), 7.25 (s, 1H), 6.99 (m, 5H), 6.65 (d, 1H, J=7.7 Hz), 5.44 (br s, 3H), 4.81 (s, 1H), 3.94 (m, 2H), 3.77 (s, 3H), 3.54 (s, 3H), 3.49 (m, 4H 3.12 (m, 8H), 2.25 (s, 3H), 2.23 (s, 3H), 1.89 (m, 2H), 1.22 (m, 2H), and 0.82 (t, 3H, J=7.4 Hz); $^{13}$C NMR (DMSO-d$_6$) δ167.6, 167.1, 155.5, 151.8, 148.3, 145.5, 140.2, 139.1, 128.0, 123.7, 120.9, 120.0, 118.3, 116.6, 115.4, 112.0, 101.6, 101.5, 62.8, 55.4, 53.6, 51.1, 50.6, 46.9, 36.4, 30.4, 24.4, 18.8, 18.3, and 13.6. Anal. Calcd for $C_{35}H_{47}N_5O_6$•2HCl•0.1H$_2$O: C, 59.08; H, 6.98; N, 9.84. Found: C, 59.08; H, 6.95; N, 10.18.

EXAMPLE 37

1,4-Dihydro-4-[3-[[[[3-[4-(2-methoxyphenyl)-1-piperazinyl]propyl]-amino]carbonyl]amino]phenyl]-2,6-dimethyl-3,5-pyridinedicarboxylic acid, 1,1-dimethylethyl methyl ester This dihydropyridine was obtained as a colorless foam in 22% yield after purification by flash chromatography: mp 108°–116° C. (sintered); $^1$H NMR (DMSO-d$_6$) δ8.67 (s, 1H), 8.27 (s, 1H), 7.25 (d, 1H, J=8.1 Hz), 7.06 (s, 1H), 7.01 (t, 1H, J=7.8 Hz), 6.86 (m, 4H), 6.66 (d, 1H), J=7.6 Hz), 6.02 (br t, 1H, J=5.6 Hz), 4.75 (s, 1H), 3.75 (s, 3H), 3.51 (s, 3H), 3.09 (m, 2H), 2.48 (m, 4H), 2.34 (t, 2H, J=6.7 Hz), 2.23 (s, 3H), 2.19 (s, 3H), 1.59 (m, 2H), and 1.33 (s, 9H); $^{13}$C NMR (DMSO-d$_6$) δ167.5, 166.6, 155.2, 152.0, 148.5, 145.5, 144.0, 141.3, 128.0, 122.3, 120.8, 120.1, 117.9, 116.7, 115.4, 103.4, 101.2, 78.7, 55.5, 55.3, 53.1, 50.6, 50.1, 37.4, 28.0, 27.0, and 18.3. Anal. Calcd for $C_{35}H_{47}N_5O_6$•0.39H$_2$O: C, 65.61; H, 7.52; N, 10.93. Found: 65.62; H, 7.30; N, 10.84.

EXAMPLE 38

1,4-Dihydro-4-[3-[[[[3-[4-(2-methoxyphenyl)-1-piperazinyl]propyl]-amino]carbonyl]amino]phenyl]-2,6-dimethyl-5-(3-methyl-1,2,4-oxadiazol-5-yl)-3-pyridine carboxylic acid, methyl ester hydrochloride salt This material was prepared using the general 3-chloropropyl isocyanate method in 25% yield after flash chromatography (SiO$_2$: ammoniated MeOH/EtOAc), conversion to the HCl salt and trituration of the salt in acetone: mp 201°–202° C.; $^1$H NMR (DMSO-d$_6$) δ10.60 (br s, 1H), 9.31 (s, 1H), 8.78 (s, 1H), 7.26 (d, 1H, J=8.1 Hz), 7.18 (s, 1H), 6.98 (m, 6H), 5.00 (s, 1H), 3.77 (s, 3H), 3.58 (s, 3H), 3.54 (m, 4H), 3.10 (m, 4H), 2.40 (s, 3H), 2.27 (s, 3H), 2.23 (s, 3H), and 1.87 (m, 2H); $^{13}$C NMR (DMSO-d$_6$) δ175.9, 167.2, 166.3, 157.1, 155.5, 151.8, 147.3, 145.4, 143.7, 140.4, 139.2, 128.4, 123.6, 120.9, 119.8, 118.3, 116.4, 115.7, 112.0, 101.2, 95.8, 55.4, 53.5, 51.1, 50.8, 46.9, 39.2, 36.4, 24.4, 18.2, 11.3. HRMS. Calcd for C$_{33}$H$_{42}$N$_7$O$_5$ (M+H): 616.3247. Found: 616.3228.

EXAMPLE 39

5-Cyano-1,4-dihydro-4-[3-[[[[3-[4-(2-methoxyphenyl)-1-piperazinyl]-propyl]amino]carbonyl]amino]phenyl]-2,6-dimethyl-3-pyridinecarboxylic acid, methyl ester This material was prepared using the general 3-chloropropyl isocyanate method in 6% yield as a colorless solid after flash chromatography (SiO$_2$: ammoniated MeOH/EtOAc): mp indistinct; $^1$H NMR (CDCl$^3$) δ7.23 (m, 4H), 6.91 (m, 5H), 6.64 (br m, 1H), 5.71 (br s, 1H), 4.53 (s, 1H), 3.82 (s, 3H), 3.52 (s, 3H), 3.25 (m, 2H), 3.01 (m, 4H 2.60 (m, 2H), 2.43 (m, 2H), 2.27 (s, 3H), 1.94 (s, 3H), and 1.68 (m, 2H). HRMS. Calcd for C$_{31}$H$_{39}$N$_6$O$_4$ (M+H): 559.3033. Found: 559.3046.

EXAMPLE 40

1,4-Dihydro-4-[3-[[[[3-[4-(2-methoxyphenyl)-1-piperazinyl]-1-propyl]-amino]carbonyl]amino]-4-chlorophenyl]-2,6-dimethyl-3,5-pyridine-dicarboxylic acid, ethyl methyl ester, hydrochloride salt A solution of 1-(3-aminopropyl)-4-(2-methoxyphenyl) piperazine$^{19}$ (5.0 mmol) in 20 mL of MeCN was added dropwise to a stirred solution of 1,1'-carbonyldiimidazole (CDI, 7.5 mmol) in 20 mL of MeCN at 0° C. The mixture was stirred for 30 min and then allowed to warm to room temperature and stir for 1 h. The reaction mixture was then partitioned between CH$_2$Cl$_2$ (50 mL) and ice water (3×50 mL), and the organic extract dried over Na$_2$SO$_4$ and solvent removed in vacuo to yield the CDI-amine adduct as a colorless oil (90% yield). A mixture of aniline (IV; 4.3 mmol) and the CDI-N-3-aminopropylpiperazine adduct (4.3 mmol) in 10 mL MeCN was refluxed for 20 h and then concentrated in vacuo. The residue was taken up in CH$_2$Cl$_2$ and washed with H$_2$O and brine and then dried over MgSO$_4$. The crude material was purified by flash chromatography and the resulting free base converted to the HCl salt. Crystallization of the salt from MeOH/Et$_2$O furnished product in 40% yield as an off-white solid: mp 161°–168° C.; $^1$H NMR (CD$_3$OD) δ7.87 (d, 1H), 7.29–6.88, (m, 7H), 4.93 (s, 1H), 4.05 (q, 2H), 3.91 (s, 3H), 3.60 (s, 3H), 3.74–3.29 (m, 12H), 2.29 (s, 6H), 2.05 (br s, 2H), and 1.20 (t, 3H). Anal. Calcd for C$_{33}$H$_{42}$N$_5$O$_6$Cl•2HCl•2H$_2$O: C, 52.91; H, 6.46; N, 9.35. Found: C, 53.08; H, 6.06; N, 9.61.

EXAMPLE 41

1,4-Dihydro-4-[3-[[[[3-[4-(2-methoxyphenyl)-1-piperazinyl]-1-propyl]-amino]carbonyl]amino]-4-(2-propenyloxy)phenyl]-2,6-dimethyl-3,5-pyridine-dicarboxylic acid, dimethyl ester hydrochloride salt This compound was prepared from amine (IV) using the general 3-chloropropyl isocyanate method. The material was obtained in 32% yield after purification by flash chromatography (SiO$_2$: ammoniated MeOH/EtOAc) and then converted to the HCl salt. The salt was crystallized from acetone/Et$_2$O to afford the product (I), R$^5$=allyloxy as a colorless solid: mp 145°–160° C. (sintered); $^1$H NMR (DMSO-d6) δ8.89 (br s, 1H), 8.00 (s, 1H), 7.70 (s, 1H), 7.14 (br s, 1H), 6.93 (m, 5H), 6.75 (d, 1H, J=8.3 Hz), 6.56 (d, 1H), 6.03 (m, 1H), 5.39 (d, 1H), 5.24 (d, 1H), 4.79 (s, 1H), 4.54 (m, 2H), 3.54 (s, 6H), 3.33 (s, 3H), 3.16 (m, 1 OH), 2.23 (s, 6H), and 1.88 (m, 2H). Anal. Calcd for C$_{35}$H$_{45}$N$_5$O$_7$•1.3HCl: C, 60.41; H, 6.71; N, 10.06. Found: C, 60.41; H, 6.52; N, 9.71.

EXAMPLE 42

1,4-Dihydro-4-[4-hydroxy-3-[[[[3-[4-(2-methoxyphenyl)-1-piperazinyl]-1-propyl]amino]carbonyl]amino]phenyl]-2,6-dimethyl-3,5-pyridinedicarboxylic acid, dimethyl ester A suspension of the allyloxy derivative (Example 49; 1.58 mmol), PdCl$_2$ (1.9 mmol), NaOAc (4.1 mmol) in 5 mL of glacial HOAc and 2 mL of H$_2$O was stirred at room temperature for 5 days. The HOAc and H$_2$O were removed in vacuo and the resulting residue then taken up in EtOAc and washed with H$_2$O, 10% aq NH$_4$OH, and brine and then dried over Na$_2$SO$_4$. After filtration, the volatiles were removed in vacuo. The crude material was purified by flash chromatography (SiO$_2$: ammoniated MeOH/EtOAc) and then converted to the HCl salt to furnish product (I), R$^5$=OH in 60% yield as a brown solid: mp indistinct; $^1$H NMR (DMSO-d$_6$) δ11.06 (br s, 1H), 8.93 (br s, 1H), 7.60 (s, 1H), 6.99 (m, 6H), 6.60 (d, 1H), 6.50 (d, 1H), 4.74 (s, 1H), 3.77 (s, 6H), 3.48 s, 3H), 3.42 (m, 2H), 3.12 (m, 10H), 2.22 (s, 6H), and 1.89 (m, 2H). HRMS. Calcd for C$_{32}$H$_{41}$N$_5$O$_7$Na (M+Na): 630.2904. Found: 630.2914.

EXAMPLE 43

1,4-Dihydro-4-[3-[[[[2-[4-(2-methoxyphenyl)-1-piperazinyl]ethyl]-amino]carbonyl]amino]phenyl]-2,6-dimethyl-3,5-pyridinedicarboxylic acid, ethyl methyl ester This compound was prepared using 2-chloroethylisocyanate followed by treatment with N-(2-methoxyphenyl)piperazine. The Formula (I) product was obtained as a white solid in 10% yield after purification by flash chromatography (SiO$_2$: MeOH/CH$_2$Cl$_2$): mp 100°–108° C.; $^1$H NMR (DMSO-$d_6$): δ8.80 (s, 1H), 8.50 (s, 1H), 7.24 (d, 1H, J=8.1 Hz), 7.08 (s, 1H), 7.01 (t, 1H, J=7.8Hz), 6.91 (m, 2H), 6.87 (m, 2H), 6.66 (d, 1H, J=7.8Hz), 5.98 (m, 1H), 4.81 (s, 1H), 3.99 (m, 2H), 3.75 (s, 3H), 3.52 (s, 3H), 3.20 (m, 2H), 2.97 (br s, 4H), 2.53 (br s, 4H), 2.42 (m, 2H), 2.24 (s, 3H), 2.23 (s, 3H), and 1.13 (t, 3H, J=7.2 Hz); $^{13}$C NMR (DMSO-$d_6$): δ167.5, 167.0, 155.1, 152.0, 148.3, 145.5, 145.2, 141.2, 140.3, 128.1, 122.4, 120.8, 120.0, 117.8, 116.5, 115.4, 111.9, 101.8, 101.4, 59.0, 57.5, 55.3, 53.0, 50.7, 50.0, 18.3, 18.2, and 14.2. Anal. Calcd for $C_{32}H_{41}N_5O_6$·0.7$H_2O$: C, 63.60; H, 7.07; N, 11.59. Found: C, 63.62; H, 6.96; N, 11.47.

EXAMPLE 44

1,4-Dihydro-4-[3-[[[[4-[4-(2-methoxyphenyl-1-piperazinyl]butyl]amino]carbonyl]amino]phenyl]-2,6-dimethyl-3,5-pyridinedicarboxylic acid, ethyl methyl ester A solution of 1-(4-aminobutyl)-4-(2-methoxyphenyl)piperazine$^{20}$ (5.0 mmol) in 20 mL of MeCN was added dropwise to a stirred solution of CDI (7.5 mmol) in 20 mL of MeCN at 0° C. The mixture was stirred at 0° C. for 30 min and then at room temperature for 1 h. The reaction mixture was then partitioned between $CH_2Cl_2$ (50 mL) and ice water (3×50 mL), and the organic extract dried over $Na_2SO_4$ and solvent removed in vacuo to yield 1-[4-[[(1-imidazolyl)carbonyl]amino]butyl]-4-(2-methoxyphenyl)piperazine as a colorless oil in 90% yield. This material was not fully characterized. It was immediately taken up in 40 mL of MeCN and aniline (IV) (4.5 mmol) was added. After refluxing for 48 h the MeCN was removed in vacuo, and the residue partitioned between $CH_2Cl_2$ and $H_2O$. The organic extract was dried over $Na_2SO_4$ and solvent removed in vacuo. The residue was subjected to flash chromatography ($SiO_2$: MeOH/$CH_2Cl_2$) to give product (I) as a white solid in 32% yield: mp 65°–75° C.; $^1$H NMR (DMSO-$d_6$): δ8.80 (s, 1H), 8.25 (s, 1H), 7.23 (d, 1H, J=9.0 Hz), 7.07 (s, 1H), 7.01 (t, 1H, J=7.8 Hz), 6.92 (m, 2H), 6.85 (m, 2H), 6.66 (d, 1H, J=7.8 Hz), 6.01 (t, 1H, J=5.4 Hz), 4.81 (s, 1H), 3.98 (m, 2H), 3.75 (s, 3H), 3.53 (s, 3H), 3.05 (m, 2H), 2.93 (br s, 4H), 2.49 (br s, 4H), 2.31 (m, 2H), 2.24 (s, 3H), 2.23 (s, 3H), 1.43 (m, 4H), and 1.13 (t, 3H, J=6.9 Hz); 13C NMR (DMSO-$d_6$): δ167.5, 167.0, 155.2, 152.0, 148.3, 145.5, 145.2, 141.3, 140.3, 128.1, 122.3, 120.8, 120.0, 117.9, 116.5, 115.4, 111.9, 101.8, 101.4, 59.0, 57.6, 55.3, 53.0, 50.6, 50.1, 27.7, 23.7, 18.3, and 14.2. HRMS. Calcd for $C_{34}H_{46}N_5O_6$ (M+H): 620.3448; Found: 620.3434.

EXAMPLE 45

1,4-Dihydro-2,6-dimethyl-4-[3-[[[[4-(2-phenoxyphenyl)-1-piperazinyl]propyl]amino]carbonyl]amino]phenyl]-3,5-pyridinedicarboxylic acid, dimethyl ester dihydrochloride This compound was obtained as a light amber solid in 45% yield: mp 75°–80° C.; $^1$H NMR (DMSO-$d_6$) δ10.67 (br s, 1H), 8.94 (s, 1H), 8.72 (s, 1H), 7.33 (t, 2H, J=7.8 Hz), 7.25 (d, 1H, J=8.1 Hz), 7.07 (M, 6H), 6.90 (m, 3H), 6.63 (d, 1H, J=7.8 Hz), 6.46 (br s, 1H), 4.82 (s, 1H), 3.53 (s, 6H), 3.49 (m, 4H), 3.07 (m, 6H), 2.88 (M, 2H), 2.23 (s, 6H), and 1.82 (m, 2H); $^{13}$C NMR (DMSO-$d_6$) δ167.5, 156.7, 155.5, 148.2, 148.1, 145.6, 141.8, 140.2, 129.9, 128.2, 124.8, 123.6, 122.9, 120.6, 119.7, 117.4, 116.5, 115.5, 101.3, 53.5, 51.1, 50.6, 46.8, 38.3, 36.3, 24.4, and 18.2. Anal calcd for $C_{37}H_{43}N_5O_6$·2 HCl·$H_2O$: C, 59.68; H, 6.36; N, 9.40. Found: C, 59.53; H, 6.42; N, 9.10.

EXAMPLE 46

4-[3-[[[[3-[Hexahydro-4-(2-methoxyphenyl)-1H-1,4-diazepin-1-yl]-propyl]amino]carbonyl]amino]phenyl]-1,4-dihydro-2,6-dimethyl-3,5-pyridine-dicarboxylic acid, dimethyl ester, hydrochloride salt This compound was isolated as an off-white solid in 9% yield: mp 125°–150° C.; $^1$H NMR (DMSO-$d_6$) δ10.29 (br s, 1H), 8.95 (s, 1H), 8.74 (s, 1H), 7.27 (d, 1H, J=8.2 Hz), 7.10 (s, 1H), 7.01 (t, 1H, J=7.8 Hz), 6.88 (m, 4H), 6.65 (d, 1H, J=7.6 Hz), 6.50 (br t, 1H), 4.83 (s, 1H), 3.78 (s, 3H), 3.54 (s, 6H), 3.36 (m, 4H), 3.15 (m, 4H), 2.25 (s, 6H), 2.20 (m, 2H), and 1.89 (m, 2H); $^{13}$C NMR (DMSO-$d_6$) δ167.4, 155.5, 151.3, 148.1, 145.6, 141.3, 140.2, 128.2, 121.6, 120.6, 119.7, 117.6, 116.4, 115.4, 111.8, 101.3, 55.4, 54.1, 55.2, 50.6, 49.2, 48.0, 36.4, 25.0, 23.7, 18.2, and 15.1. Anal Calcd for $C_{33}H_{43}N_5O_6$·1.5HCl: C, 59.93; H, 6.79; N, 10.59. Found: C, 59.93; H, 6.70; N, 10.37.

Additional examples of products of the instant invention are given in Table 1. These additional compounds are synthesized using the above-described procedures.

TABLE 1

Additional Formula I Products

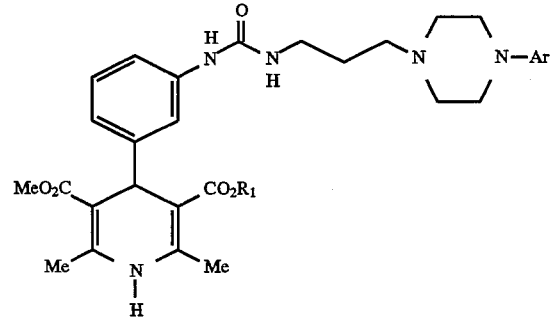

| Ex. No. | $R_1$ | Ar | mp °C. |
|---|---|---|---|
| 47 | Et | $CH_2$Ph | 50–60 |
| 48 | Et | Ph | 65–75 |
| 49 | Et | 2-MePh | 80–84* |
| 50 | Et | 4-MePh | 113–118* |
| 51 | Et | 4-ClPh | 149–152* |
| 52 | Et | 3,4-$Cl_2$Ph | 116–126* |
| 53 | Et | 4-MeOPh | 108–110* |
| 54 | Et | 2-($C_3H_5$O)Ph$^c$ | 173–184* |
| 55 | Et | 2-($C_3H_7$O)Ph$^d$ | 180–188* |
| 56 | Et | 2-HOPh | 188–222* |
| 57 | Et | 3-HOPh | 90–95** |
| 58 | Me | 3-HOPh | 93–98* |
| 59 | Et | 4-$H_2$NPh | 103–105* |
| 60 | Et | 2-$MeO_2$CPh | 55–60** |
| 61 | Et | 2-$H_2$N-4-$CF_3$Ph | >95°** |
| 62 | Et | 2-HCONH-4-$CF_3$Ph | 195–248*** |
| 63 | Me | 3-MeOPh | 93–98* |

*dihydrochloride salt
**maleic acid salt
***monohydrochloride salt
****fumaric acid salt
$^c$2-propenyloxyphenyl
$^d$2-propyloxyphenyl Chart 1. Competitive Non-Peptidic NPY Antagonists
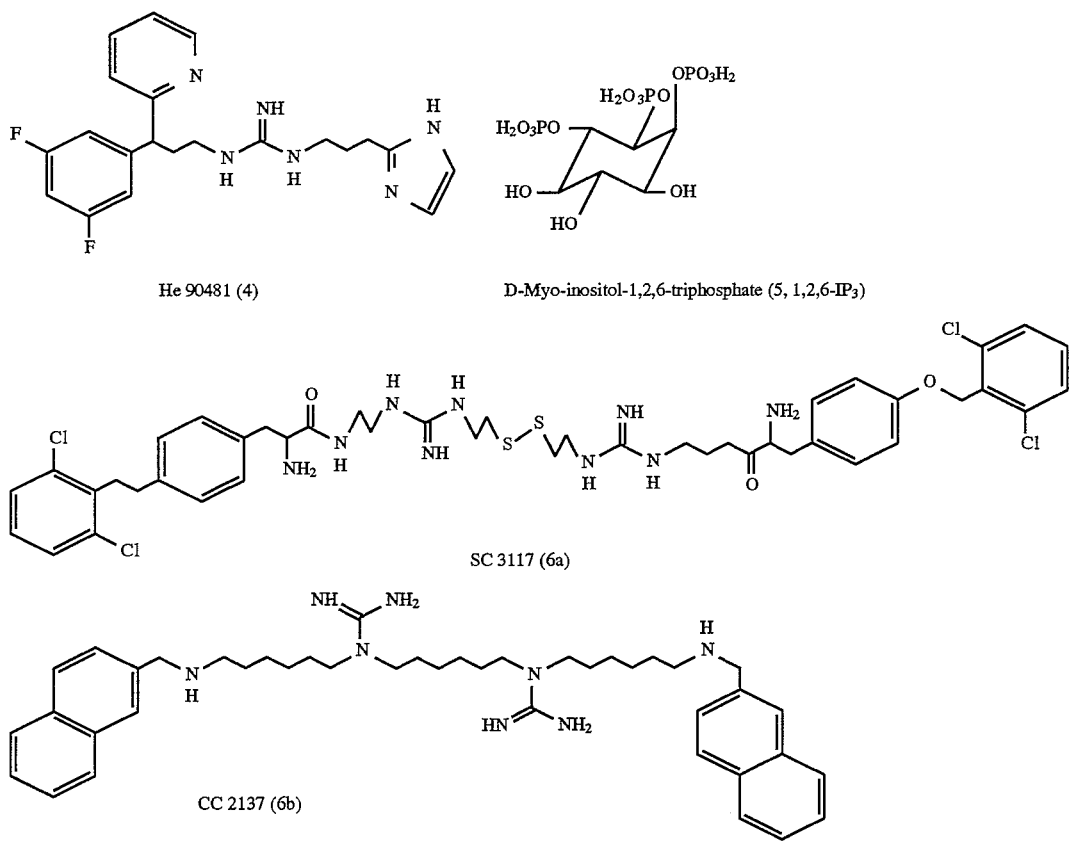
He 90481 (4)
D-Myo-inositol-1,2,6-triphosphate (5, 1,2,6-IP$_3$)
SC 3117 (6a)
CC 2137 (6b)
Chart 2. Selective Non-Peptidic NPY Antagonists
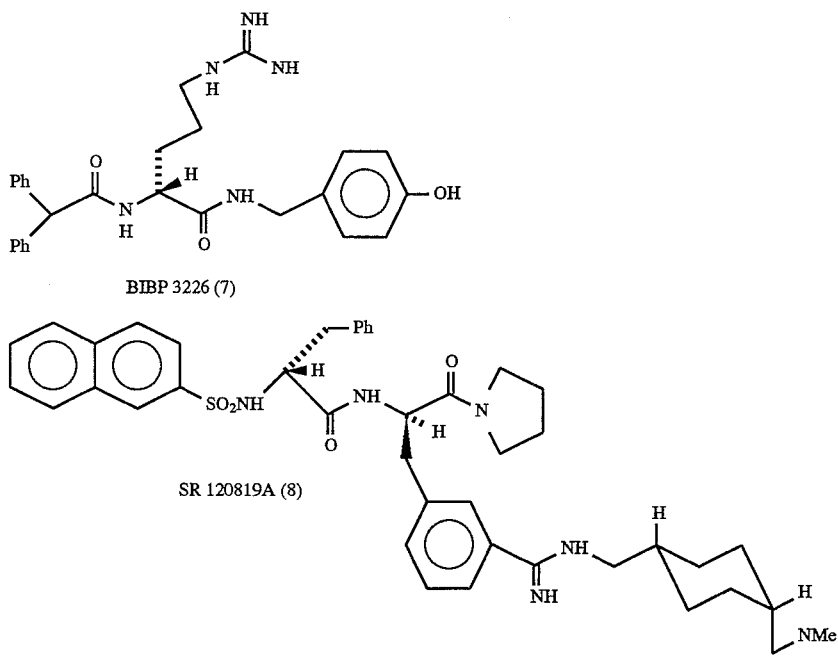
BIBP 3226 (7)
SR 120819A (8)

Scheme 1
General Processes for Compound (I)
Synthesis: Anilide-Linked Derivatives
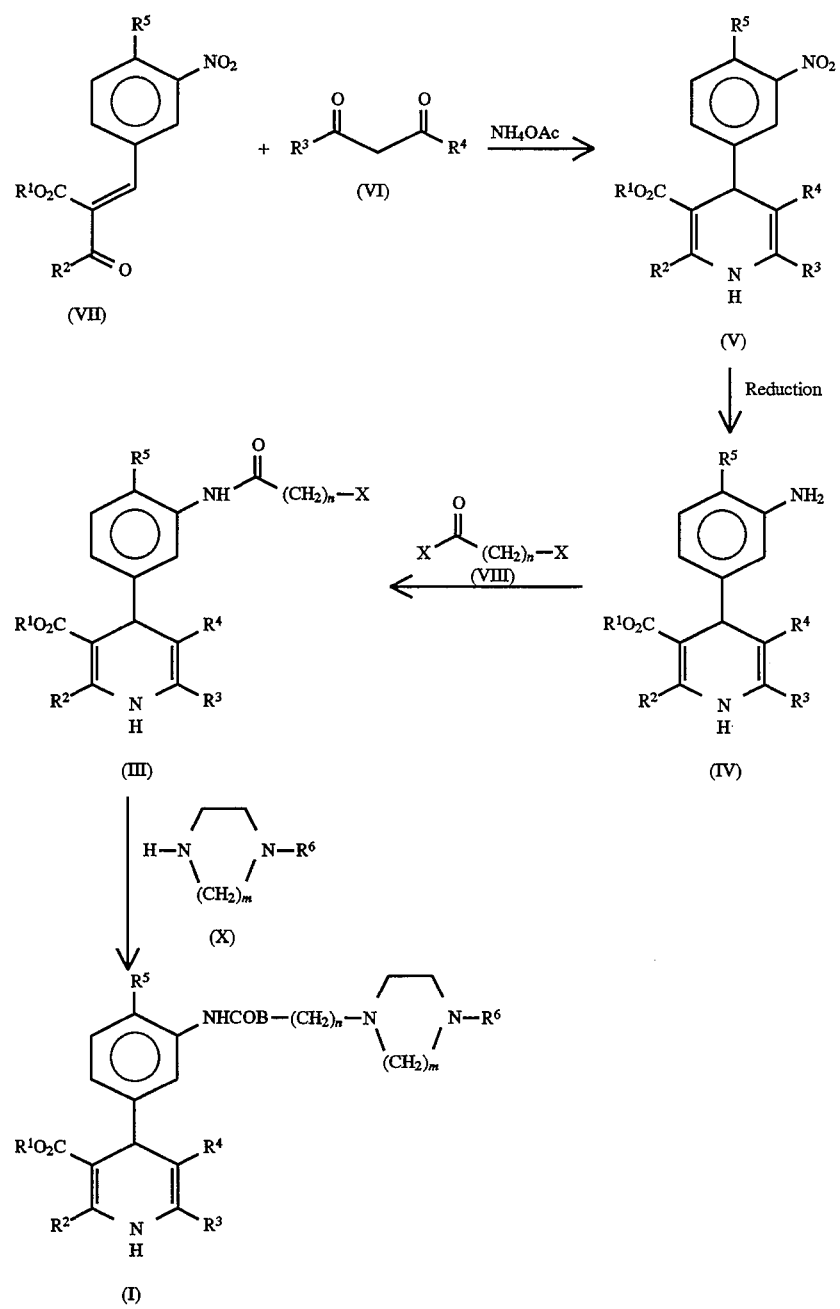

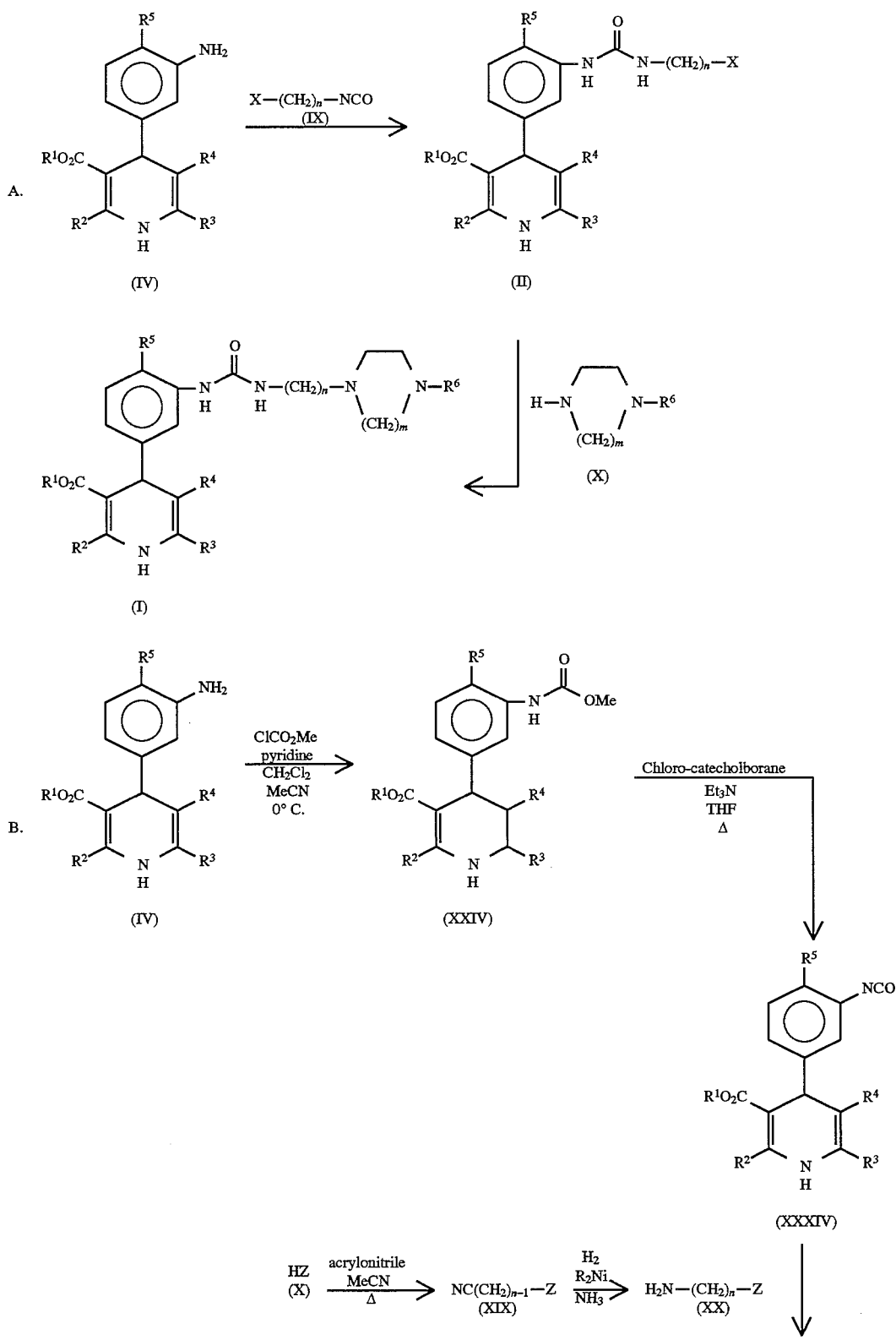

-continued
Scheme 2
General Processes for Compound (I)
Synthesis: Urea-Linked Derivatives
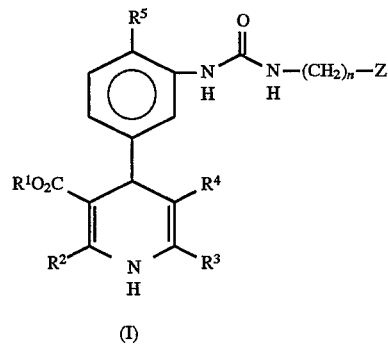
(I)
Scheme 3
Modified Processes for Compound (V) Synthesis
A. $R^2$ and/or $R^3$ = CN:
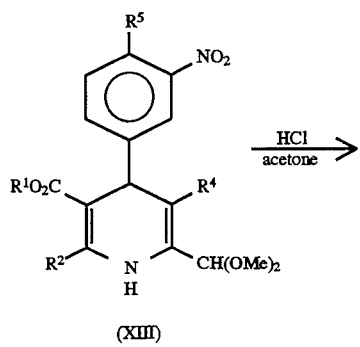
(XIII)
$\xrightarrow{\text{1) HONH}_2}{\text{2) Ac}_2\text{O}}$
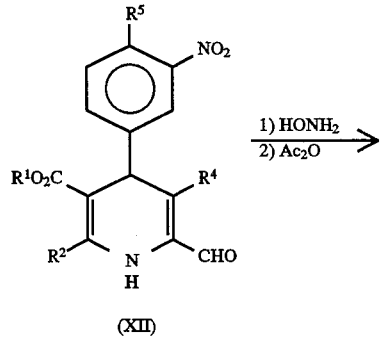
(XII)
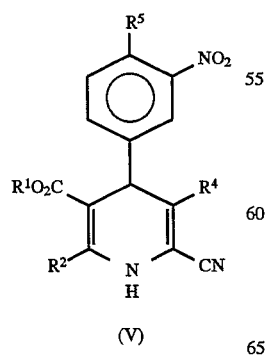
(V)
-continued
Scheme 3
Modified Processes for Compound (V) Synthesis
B. $R^4 =$ 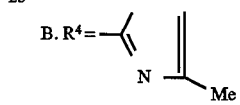
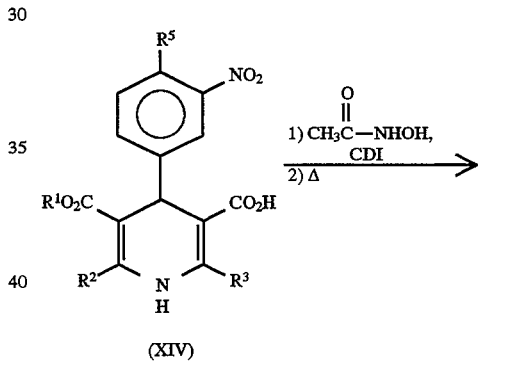
(XIV)
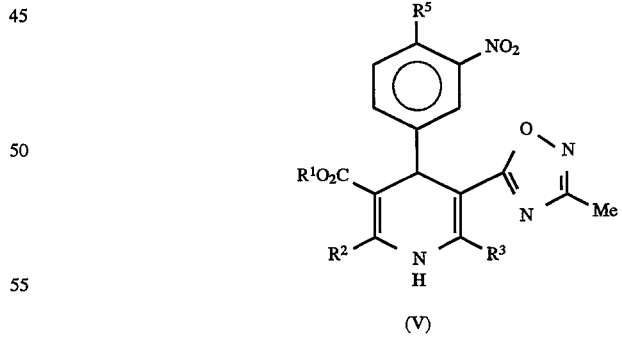
(V)

Scheme 4
Specific Syntheses for Selected Compounds of Formula (I)
A. $R^5 = OH$:
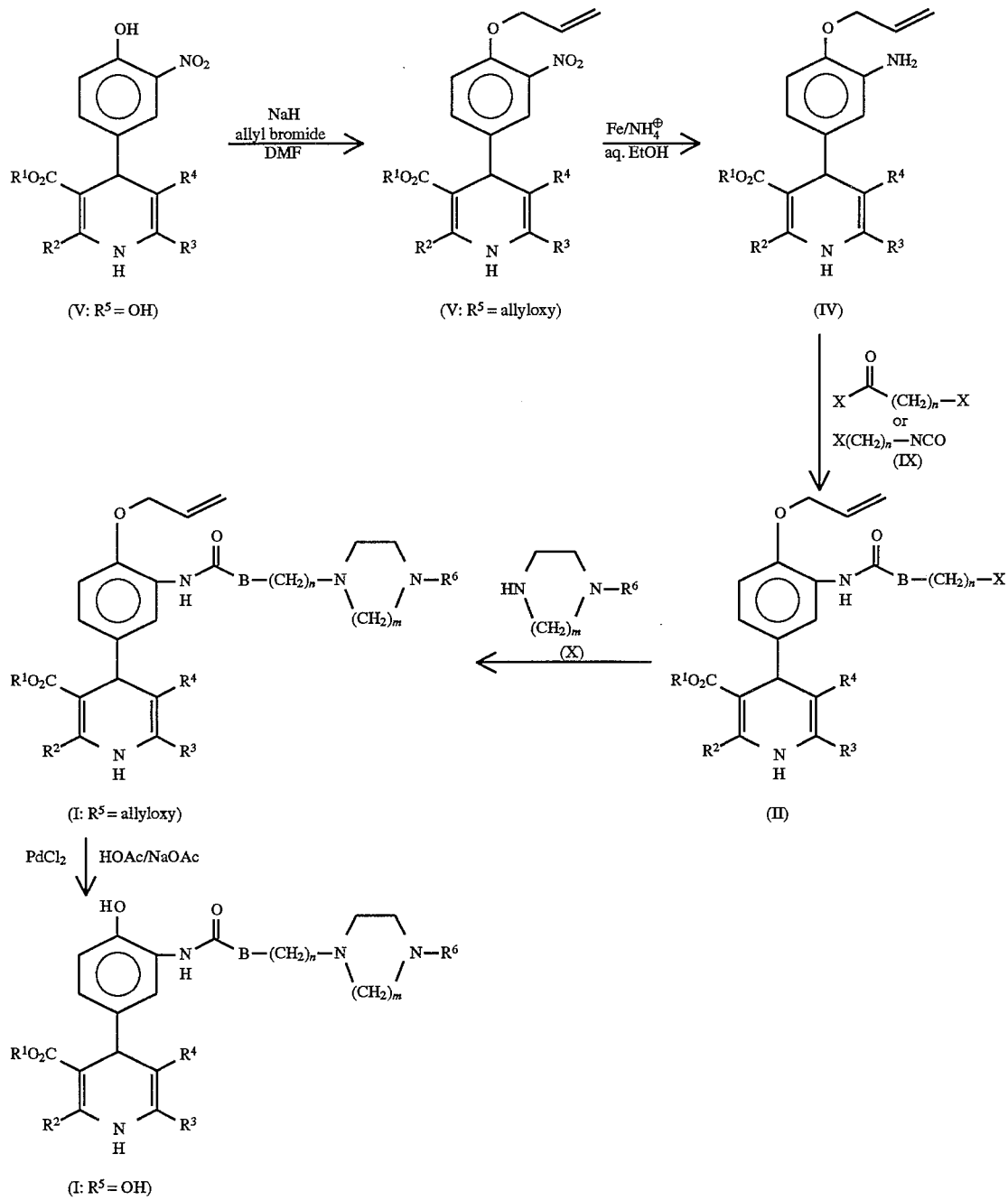

Scheme 5
Synthesis of a Formula (X) Compound

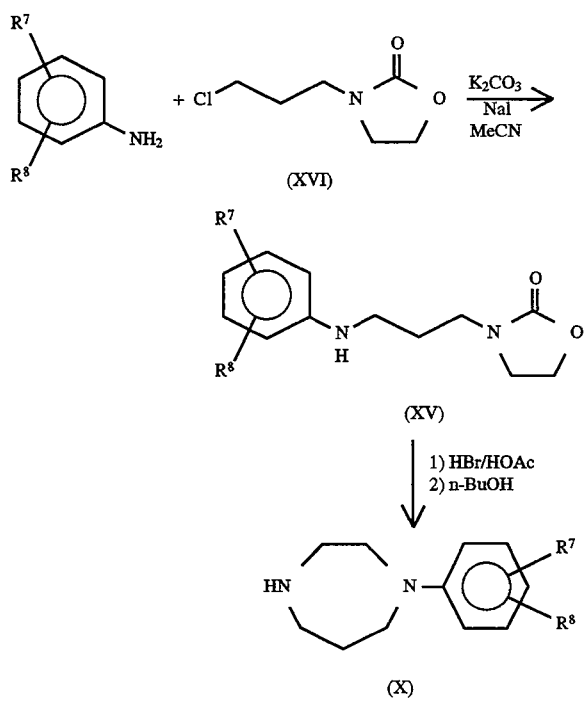

References and Notes

1. K. Takemoto, *Proc. Nat. Acad. Sci.*, 1982, 79, 5485–5489.
2. 
   (a) D. R. Gehlert, *Life Sciences*, 1994, 55, 551–62.
   (b) L. Grundemar and R. Hakånson, *TIPS*, 1994, 15, 153–159.
   (c) C. Wahlestedt and D. J. Reis, *Ann. Rev. Pharmacol. Toxicol.*, 1993, 32, 309–352.
   (d) J. D. White, *Regulatory Peptides*, 1993, 49, 93–107.
   (e) A. Sahu and S. P. Kalra, *Trends Endocrinol. Metab.*, 1993, 4, 217–224.
   (f) Y. Dumont, J.-C. Martel, A. Fournier, S. St. Pierre and R. Quidon, *Prog. Neurobiol.* 1992, 38, 125–167.
   (g) M. C. Michel and A. Buscher, *Drugs of the Future*, 1992, 17, 39–45.
   (h) M. C. Michel, *TIPS*, 1991, 12, 389–394.
   (i) J. Lehmann, *Drug. Dev. Res.*, 1990, 19, 329–351.
3. M. C. Michel and H. J. Motulsky, *Annu. Rev. N.Y. Acad. Sci.*, 1990, 611, 392–394; U.S. Pat. No. 4,912,119, 1990 (Heumann Pharma GMBH).
4. L. Edvinsson, M. Adamsson and I. Jansen, *Neuropeptides*, 1990, 17, 99–105.
5. 
   (a) M. B. Doughty, C. Chaurasia and K. Li, *J. Med. Chem.*, 1993, 36, 272–79.
   (b) M. B. Doughty, S. S. Chu, G. A. Misse and R. Tessel, *BioMed. Chem. Lett.*, 1992, 2, 1497–1502.
   (c) C. Chaurasia, G. Misse, R. Tessel and M. B. Doughty, *J. Med. Chem.*, 1994, 37, 2242–48.
6. K. Rudolf, W. Eberlein, H. A. Wieland, K. D. Willim, M. Entzeroth, W. Wienen, A. G. Beck-Sicklinger and H. N. Doods, *Eur. J. Pharmacol.*, 1994, 271, R11–R13.
7. C. Serradeil-LeGal, G. Valette, P.-E. Rouby, A. Pellet, F. Oury-Donat, G. Brossard, L. Lespy, E. Marty, G. Neliat, P. deCointet, J.-P. Maffrand and G. LeFur, *FEBS Lett.*, 1995, 362, 192–196.
8. 
   (a) A. Sausins and G. Duburs, *Heterocycles*, 1988, 27, 269.
   (b) D. M. Stout and A. I. Meyers, *Chem. Review.*, 1982, 82, 223.
   (c) J. Kuthan and A. Kurfurst, *Ind. Eng. Chem. Prod. Res. Dev.*, 1982, 21, 191.
   (d) U. Eisner and J. Kuthan, *J. Chem. Rev.*, 1972, 72, 1.
   (e) J. Prous, P. Biancafort, J. Castafter, M. N. Serradell and N. Mealy, *Drugs of the Future*, 1981, 6, 427.
9. G. Jones, *Org. Reactions*, 1967, 15, 204.
10. 
    (a) V. H. Meyer, F. Bossert, E. Wehinger, K. Stoepel and W. Vater, *Arzneim.-Forsch/Drug Research*, 1981, 31,407.
    (b) A. F. Joslyn, E. Luchowski, D. J. Triggle, *J. Med. Chem.*, 1988, 31, 1489–1492.
    (c) R. A. Coburn, M. Wierzba, M. J. Suto, A. J. Solo, A. M. Triggle, D. J. Triggle, *J. Med. Chem.*, 1988, 31, 2103, 2107.
    (d) E. Wehinger, U.S. Pat. No. 4,920,255, 1981.
    (e) U. Rosentreter, *Synthesis*, 1985, 210.
    (f) F. Bossert, H. Horstmann, H. Meyer, W. Vater, *Arzneim.-Forsch.*, 1979, 29, 226–229.
    (g) R. B. Hargreaves, B. J. McLoughlin, S. D. Mills, Eur. Pat. Appl. EP 194751, 1986.
    (h) *Chem. Abstr.*, 1985, 103, 123313g.
11. N. M. Yoon and J. S. Choi, *S. Synlett*, 1993, 135–136.
12. 
    (a) F. Bossert and W. Vater, S. African Patent 01,482, 1968.
    (b) D. Scherling, W. Karl, A. J. Ahr, A. Kern and H. M. Siefert, *Arzneim.-Forsch.*, 1991, 41, 1009–1021.
13. Y. Satoh, et al, *Chem. Pharm. Bull.*, 1991, 39, 3189–3201.
14. E. Wehinger, U.S. Pat. No. 4,920,255, 1981.
15. K. Ramadas and N. Srinivasan, *Syn. Commun.*, 1992, 22, 3189–3195.
16. R. A. Stokbroeker, M. J. M. Van den Aa, J. J. M. Willems, M. J. M. Luyckx, Eur. Patent Appln. EP 156, 433, 1985.
17. K. Schonafinger, H. Bohn, M. Just, and P. Martaranna, U.S. Pat. No. 4,558,058, 1985.
18. G. S. Poindexter, M. A. Bruce, K. L. LeBoulluec and I. Monkovic, *Tetrahedron Lett.*, 1994, 35, 7331.
19. Y.-H. Wu, K. R. Smith and J. W. Rayburn, *J. Med. Chem.*, 1969, 12, 876–881.
20. R. A. Glennon, N. A. Naiman, R. A. Lyon and M. Titeler, *J. Med. Chem.*, 1988, 31, 1968–1971.
21. C. Wahlestedt and D. J. Reis, *Annual Rev. Pharmacol. Toxicol.*, 1993, 32:309–52; p. 331.
22. V. L. K. Valli and H. Alper, *J. Org. Chem.*, 1995, 60:257–258.

We claim:

1. A compound of Formula (I) or its pharmaceutically acceptable

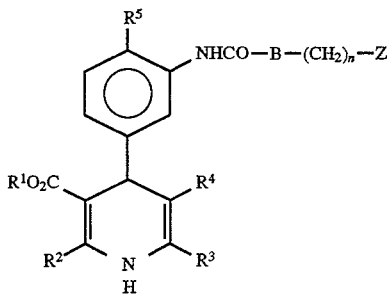 (I)

acid addition salts or hydrates thereof, wherein $R^1$ is lower alkyl;

$R^2$ and $R^3$ are independently selected from cyano and lower alkyl;

$R^4$ is selected from —$CO_2R^1$, cyano and

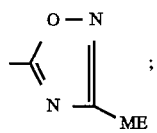

$R^5$ is selected from hydrogen, halogen, hydroxy, lower alkyl, lower alkenyloxy, and lower alkoxy;

B is —NH— or a covalent bond except when $R^4$ is cyano;

n is an integer selected from 2 to 5; and

Z is

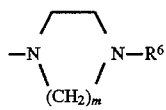

in which m is the integer 2 or 3;

$R^6$ is selected from formyl, lower alkyl, phenyl-lower-alkyl,

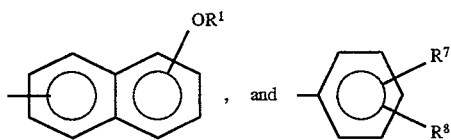

with $R^7$ and $R^8$ being independently selected from hydrogen, lower alkyl, $C_{3-7}$ cycloalkyl, lower alkoxy, hydroxy, phenoxy, $NH_2$, $NHCOR^1$, $CO_2R^1$, $NO_2$, trifluoromethyl, and phenyl.

2. A compound of claim 1 wherein B is —NH—.
3. A compound of claim 1 wherein B is a covalent bond.
4. A compound of claim 1 wherein $R^6$ is

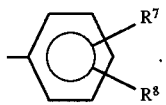

5. A compound of claim 1 wherein n is 3.
6. A compound of claim 2 selected from
1,4-Dihydro-4-[3-[[[[3-[4-(2-methoxyphenyl)-1-piperazinyl]propyl]amino]carbonyl]amino]phenyl]-2,6-dimethyl-3,5-pyridinedicarboxylic acid, ethyl methyl ester;

2-Cyano-1,4-dihydro-4-[3-[[[[3-[4-(2-methoxyphenyl)-1-piperazinyl]propyl]amino]carbonyl]amino]phenyl]-6-methyl-3,5-pyridinedicarboxylic acid, 3-ethyl-5-methyl ester;

1,4-Dihydro-4-[3-[[[[3-[4-(2-methoxyphenyl)-1-piperazinyl]propyl]amino]carbonyl]amino]phenyl]-2,6-dimethyl-3,5-pyridinedicarboxylic acid, diethyl ester;

1,4-Dihydro-4-[3-[[[[3-[4-(2-methoxyphenyl)-1-piperazinyl]propyl]amino]carbonyl]amino]phenyl]-2,6-dimethyl-3,5-pyridinedicarboxylic acid, dimethyl ester;

1,4-Dihydro-4-[3-[[[[3-[4-(2-methoxyphenyl)-1-piperazinyl]propyl]amino]carbonyl]amino]phenyl]-2,6-dimethyl-5-(3-methyl-1,2,4-oxadiazol-5-yl)-3-pyridinedicarboxylic acid, methyl ester;

1,4-Dihydro-4-[4-hydroxy-3-[[[[3-[4-(2-methoxyphenyl)-1-piperazinyl]-1-propyl]amino]carbonyl]amino]phenyl]-2,6-dimethyl-3,5-pyridine-dicarboxylic acid, dimethyl ester;

1,4-Dihydro-4-[3-[[[[2-[4-(2-methoxyphenyl)-1-piperazinyl]ethyl]amino]carbonyl]amino]phenyl]-2,6-dimethyl-3,5-pyridinedicarboxylic acid, ethyl methyl ester;

1,4-Dihydro-4-[3-[[[[4-[4-(2-methoxyphenyl)-1-piperazinyl]butyl]amino]carbonyl]amino]phenyl]-2,6-dimethyl-3,5-pyridinedicarboxylic acid, ethyl methyl ester;

1,4-Dihydro-4-[3-[[[[3-[4-(phenylmethyl)-1-piperazinyl]propyl]amino]carbonyl]amino]phenyl]-2,6-dimethyl-3,5-pyridinedicarboxylic acid, ethyl methyl ester;

1,4-Dihydro-2,6-dimethyl-4-[3-[[[[3-(4-phenyl-1-piperazinyl)propyl]amino]carbonyl]amino]phenyl]-3,5-pyridinedicarboxylic acid, ethyl methyl ester;

1,4-dihydro-2,6-dimethyl-4-[3-[[[[3-[4-(2-methylphenyl)-1-piperazinyl]propyl]amino]carbonyl]amino]phenyl]-3,5-pyridinedicarboxylic acid, ethyl methyl ester;

4-[3-[[[[3-[4-(4-Chlorophenyl)-1-piperazinyl]propyl]amino]carbonyl]amino]phenyl]-1,4-dihydro-2,6-dimethyl-3,5-pyridinedicarboxylic acid, ethyl methyl ester;

1,4-Dihydro-2,6-dimethyl-4-[4-[[[[3-[4-(2-propenyloxyphenyl)-1-piperazinyl]propyl]amino]carbonyl]amino]phenyl]-3,5-pyridinedicarboxylic acid, ethyl methyl ester;

1,4-Dihydro-2,6-dimethyl-4-[4-[[[[3-[4-(2-propyloxyphenyl)-1-piperazinyl]propyl]amino]carbonyl]amino]phenyl]-3,5-pyridine dicarboxylic acid, ethyl methyl ester;

1,4-Dihydro-4-[4-[[[[3-[4-(2-hydroxyphenyl)-1-piperazinyl]propyl]amino]carbonyl]amino]phenyl]-2,6-dimethyl-3,5-pyridinedicarboxylic acid, ethyl methyl ester, 1,4-Dihydro-4-[3-[[[[3-[4-(3-hydroxyphenyl)-1-piperazinyl]propyl]amino]carbonyl]amino]phenyl]-2,6-dimethyl-3,5-pyridinedicarboxylic acid, ethyl methyl ester, 1,4-Dihydro-4-[3-[[[[3-[4-(3-hydroxyphenyl)-1-piperazinyl]propyl]amino]carbonyl]amino]phenyl]-2,6-dimethyl-3,5-pyridinedicarboxylic acid, dimethyl ester, 4-[3-[[[[4-[(4-Aminophenyl)-1-piperazinyl]propyl]amino]carbonyl]amino]phenyl]-1,4-dihydro-2,6-dimethyl-3,5-pyridinedicarboxylic acid, ethyl methyl ester;

4-[3-[[[[3-[4-[2-(Ethoxycarbonyl)phenyl]-1-piperazinyl]propyl]amino]carbonyl]amino]phenyl]-1,4-dihydro-2,6-dimethyl-3,5-pyridinedicarboxylic acid, ethyl methyl ester;

1,4-Dihydro-4-[3-[[[[3-[4-(3-methoxyphenyl)-1-piperazinyl]propyl]amino]carbonyl]amino]phenyl]-2,6-dimethyl-3,5-pyridinedicarboxylic acid, dimethyl ester;

4-[3-[[[[3-[Hexahydro-4-(2-methoxyphenyl)-1H-1,4-diazepin-1-yl]propyl]amino]carbonyl]amino]phenyl]-1,4-dihydro-2,6-dimethyl-3,5-pyridinedicarboxylic acid, dimethyl ester; or 1,4-Dihydro-2,6-dimethyl-4-[3-[[[[3-[4-(2-phenoxyphenyl)-1-piperazinyl]propyl]amino]carbonyl]amino]phenyl]-3,5-pyridinedicarboxylic acid, dimethyl ester.

7. A compound of claim 3 selected from 1,4-Dihydro-4-[3-[[5-[4-(7-methoxynaphthalen-1-yl)-piperazin-1-yl]-1-oxo-1-pentyl]amino]phenyl]-2,6-dimethyl-3,5-pyridinedicarboxylic acid, dimethyl ester.

8. A compound of claim 6 selected from 1,4-Dihydro-4-[3-[[[[3-[4-(2-methoxyphenyl)-1-piperazinyl]propyl]amino]carbonyl]amino]phenyl]-2,6-dimethyl-3,5-pyridinedicarboxylic acid, dimethyl ester;

1,4-Dihydro-4-[3-[[[[3-[4-(3-hydroxyphenyl)-1-piperazinyl]propyl]amino]carbonyl]amino]phenyl]-2,6-dimethyl-3,5-pyridinedicarboxylic acid, dimethyl ester;

1,4-Dihydro-4-[3-[[[[3-[4-(3-methoxyphenyl)-1-piperazinyl]propyl]amino]carbonyl]amino]phenyl]-2,6-dimethyl-3,5-pyridinedicarboxylic acid, dimethyl ester;

4-[3-[[[[3-[Hexahydro-4-(2-methoxyphenyl)-1H-1,4-diazepin-1-yl]propyl]amino]carbonyl]amino]phenyl]-1,4-dihydro-2,6-dimethyl-3,5-pyridinedicarboxylic acid, dimethyl ester; or 1,4-Dihydro-2,6-dimethyl-4-[3-[[[[3-[4-(2-phenoxyphenyl)-1-piperazinyl]propyl]amino]carbonyl]amino]phenyl]-3,5-pyridinedicarboxylic acid, dimethyl ester.

9. A method of promoting weight loss and treating eating disorders in a mammal which comprises administering to a mammalian host an anorexiant effective dose of a compound claimed in claim 1.

10. A pharmaceutical composition for use in promoting weight loss and treating eating disorders comprising an anorexiant effective amount of a compound claimed in claim 1 in combination with a pharmaceutically acceptable carrier.

* * * * *